(12) United States Patent
Zhang et al.

(10) Patent No.: US 10,646,595 B2
(45) Date of Patent: May 12, 2020

(54) PORPHYRIN COMPOUNDS AND THEIR USE AS MRI CONTRAST AGENTS

(71) Applicants: THE GOVERNING COUNCIL OF THE UNIVERSITY OF TORONTO, Toronto (CA); THE HOSPITAL FOR SICK CHILDREN, Toronto (CA)

(72) Inventors: Xiao-an Zhang, Toronto (CA); Wei Ran Cheng, Toronto (CA); Inga Haedicke, Toronto (CA); Hai-Ling Cheng, Richmond Hill (CA)

(73) Assignees: THE GOVERNING COUNCIL OF THE UNIVERSITY OF TORONTO, Toronto, Ontario (CA); THE HOSPITAL FOR SICK CHILDREN, Toronto, Ontario (CA)

(\*) Notice: Subject to any disclaimer, the term of this patent is extended or adjusted under 35 U.S.C. 154(b) by 1118 days.

(21) Appl. No.: 13/765,458

(22) Filed: Feb. 12, 2013

(65) Prior Publication Data

US 2014/0227196 A1   Aug. 14, 2014

(51) Int. Cl.
*A61K 49/10* (2006.01)

(52) U.S. Cl.
CPC .................. *A61K 49/106* (2013.01)

(58) Field of Classification Search
CPC .................................................. A61K 49/10
See application file for complete search history.

(56) References Cited

U.S. PATENT DOCUMENTS

| | | | |
|---|---|---|---|
| 4,986,256 A | 1/1991 | Cohen et al. | |
| 5,262,532 A * | 11/1993 | Tweedle | C07D 487/22 424/9.362 |
| 5,493,017 A * | 2/1996 | Therien | A61K 31/555 540/145 |
| 6,479,477 B1 * | 11/2002 | Crapo | C07D 487/22 514/183 |
| 7,341,711 B2 | 3/2008 | Port | |
| 8,133,474 B2 | 3/2012 | Zhang et al. | |
| 2004/0076585 A1 * | 4/2004 | Gong | A61K 9/5123 424/9.61 |
| 2008/0311304 A1 * | 12/2008 | Thompson | B82Y 10/00 427/402 |

FOREIGN PATENT DOCUMENTS

| | | | | |
|---|---|---|---|---|
| CN | 1960042 | * | 5/2007 | ............ Y02E 60/50 |
| CN | 101298054 A | | 11/2008 | |

OTHER PUBLICATIONS

Skillman et al., JACS, 1992, 114, p. 9538-44.*
Neya et al., Biochemistry, 1998, 37(16), p. 5487-5493.*
Ohkatsu et al., Bull. Chem. Soc. Jpn., 1994, 67, p. 742-7.*
Ma et al., J. Phys. Chem. A, 2009, 113, p. 10119-10124.*
Fleischer, Inorganica Chimica Acta, 1978, 29 p. 267-271 (Year: 1978).*
Sinelshchikova et al., Inorg. Chem., 2013, 52, p. 999-1008. (Year: 2013).*
Trova et al., Bioorganic & Medicinal Chemistry, 2003,11, p. 2695-2707. (Year: 2003).*
Chen, C.-w.; Cohen, J. S.; Myers, C. E.; Sohn, M., FEBS Lett. 1984, 168, 70.
Koenig, S. H.; Brown, R. D., III.; Spiller, M., Magn. Reson. Med. 1987, 4, 252.
Zhang, X.-a.; Lovejoy, K. S.; Jasanoff, A.; Lippard, S. J., Proc. Natl. Acad. Sci. U. S. A. 2007, 104, 10780.
Bradshaw, J. E.; Gillogly, K. A.; Wilson, L. J.; Kumar, K.; Wan, X. M.; Tweedle, M. F.; Hernandez, G.; Bryant, R. G., Inorg. Chim. Acta 1998, 276, 106.
Bryant, L. H. Jr.; Hodges, M. W.; Bryant, R. G., Inorg. Chem. 1999, 38, 1002.
Changfu et al., "Synthesis and Applications in Catalysis of Porphyrinic Metal-Organic Frameworks," Progress in Chemistry, 2014 26(2/3): pp. 277-292 (English Abstract).
Sigma-Aldrich, "4,4',4",4'"—(Porphine-5, 10, 15, 20-tetrayl)tetrakis(benzoic acid), 2019, (https://www.sigmaaldrich.com/catalog/product/aldrich/379077?lang=en&region=US 1 page, 3 pages.
Sigma-Aldrich, https://www.sigmaaldrich.com/catalog/NoSearchResults.jsp, (printed Oct. 29, 2019), 1 page.
Gong, Xianchang et al, "Preparation and Characterization of Porphyrin Nanoparticles", J. Am. Chem. Soc, 124, (2002), pp. 14290-14291.

\* cited by examiner

*Primary Examiner* — Michael G. Hartley
*Assistant Examiner* — Leah H Schlientz
(74) *Attorney, Agent, or Firm* — Hill & Schumacher

(57) ABSTRACT

Water soluble porphyrin compounds useful in the field of magnetic resonance imaging (MRI) as contrast agents. Particular compounds include manganese.

5 Claims, 3 Drawing Sheets

PORPHYRIN COMPOUNDS AND THEIR USE AS MRI CONTRAST AGENTS

FIELD OF THE INVENTION

The present invention relates to water soluble porphyrin compounds useful in the field of magnetic resonance imaging (MRI) as contrast agents.

BACKGROUND OF THE INVENTION

Developed in the 1970's[,2], MRI has rapidly grown into an indispensable and increasingly popular imaging modality. Owing to its deep tissue penetration, non-invasiveness, excellent soft tissue contrast and high spatial resolution, MRI is used for diagnosis and treatment monitoring of a wide variety of diseases.

In conventional MRI scans, signals are mainly derived from $^1$H-NMR peaks of water and fat molecules present in the body being imaged. The image contrast of the tissues is determined by a number of factors, such as proton density, spin-lattice relaxation time ($T_1$), and the spin-spin relaxation time ($T_2$). $T_1$ is a measure of how quickly the longitudinal magnetization vector ($M_z$) of spinning nuclei recovers towards the equilibrium direction after a resonant radio frequency (RF) pulse[6]. $T_2$ relaxation time is a time constant that describes the dephasing of the transverse nuclear magnetization. Since $T_1$ and $T_2$ relaxations vary from tissue to tissue, acquisition parameters can be adjusted to differentiate among tissues. For example, dipoles in fats or hydrocarbon rich environments have much shorter $T_1$ relaxation times than those in aqueous environments.

Despite its increasing number of applications, MRI is impeded by its intrinsic low detection sensitivity[7,8] compared to imaging modalities that use ionizing radiation such as Positron Emission Tomography (PET), hampering its ability to detect certain pathologies, such as small tumors or differentiating post therapy tumor progression. Governed by the thermal equilibrium polarization of the nuclei, e.g. at room temperature and magnetic field of 1.5 Tesla (T) (commonly used in most clinical MR scanners), only 5 out of 1 million $^1$H spins are polarized[9]. According to Curie's Law, macroscopic magnetization is directly proportional to the magnetic field strength[10]. Increasing the field strength can partly compensates for this loss in sensitivity and improve signal-to-noise ratio (S/N)[11]. However, other than the cost of ultrahigh field scanners (higher than 7 T), there is a major concern relating to tissue overheating due to overexposure of radio frequency[12] and technical issues such as coil design[13].

Currently, the widely applied method of increasing MRI S/N, hence contrast and specificity, is the use of relaxation contrast agents, which can accelerate the relaxation rate of surrounding waters' nuclei spins. MRI CAs are categorized into $T_1$ and $T_2$ agents. $T_1$ agents are mainly based on paramagnetic metal ions with unpaired valence electrons which can effectively shorten mainly the $T_1$ relaxation time of the nearby water nuclei via electron-nuclear spin-spin coupling[6]. Clinical $T_1$ CAs predominantly utilize Gd(III) which is chelated by different ligands to reduce the toxicity of free Gd(III) in vivo. Typical ligands include diethylene-triamine-penta-acetic acid (DTPA; Gd-DTPA is sold under the name Magnevist®) and 1,4,7,10-tetraazacyclododecane-1,4,7,10-tetraacetic acid (DOTA; Gd-DOTA is sold under the name Dotarem®) and their derivatives. $T_2$ agents, which are mostly superparamagnetic particles, disrupt the homogeneity of the magnetic field causing predominant decreases in $T_2$ and $T_2$* due to diffusion of water through field gradients. $T_1$ agents are able to generate positive contrast (increased signal intensity) in $T_1$ weighted images while $T_2$ agents such as superparamagnetic iron oxide nanoparticles (SPIONs), generate negative contrast in $T_2$ weighted images. For clinical diagnostic applications, $T_1$ agents are usually preferred because a number of natural sources (tissues with low signal intensity) also generate negative contrast, complicating the analysis of the MRI image. In fact, most FDA approved $T_2$ agents were discontinued. Therefore the focus of this patent is on $T_1$ agents.

A number of Gd-based CAs have been approved for clinical applications, such as ProHance® and Magnevist®, which are currently dominating the CA market. At least two problems exist with small Gd-based CAs. The relaxivity of Gd-based contrast agents could be higher, particularly at high magnetic fields e.g., at 3 T or higher. Further there is a problem of toxicity that results from free Gd(III) i.e., which escapes the chelating agent in certain patients with renal dysfunction. These two issues are interrelated.

Small Gd-based CAs have relatively low relaxivity (about 3-4 mM$^{-1}$ s$^{-1}$ at 1 T, 37° C.) and as a result, gram quantities are typically injected into a patient for generating an image with reasonable quality. In recent years, MRI scanners are moving to higher magnetic fields (mainly 3 T) in order to perform scans with improved signal/noise ratio, shorter acquisition times and better image resolution. Since the relaxivity of the commercially available Gd-based CAs decreases at higher magnetic fields, even larger quantities of CAs would be required for adequate contrast enhancement[14]. In addition, studies such as contrast-enhanced MR angiography and delayed contrast-enhanced myocardinal viability examinations require even higher CA doses and thus, further increase the risk of metal toxicity[15]. Although many in vitro studies have indicated that these Gd-based CAs are thermodynamically stable, the emergence and proliferation of nephrogenic systemic fibrosis (NSF) cases correlated to the usage of Gd-based CAs since the late 1990s suggests in vivo release and accumulation of toxic free Gd(III) in certain patients with renal dysfunction. Symptoms of NSF include severe skin induration, muscle restlessness and sometimes, physical disability. To address the severity of this safety issue, the FDA requires a "Black Box" warning label to be attached to all Gd-based CAs indicating possible adverse effects.

Various attempts have been made to improve the relaxivity mainly by increasing the size and thus rotational diffusion time ($T_R$) of Gd-based CAs, based on the Solomon-Bloembergen-Morgan (SBM) theory. Common strategies include attachment of Gd CAs to proteins, dendrimers or polymers. Notably, at high magnetic fields (>1.5 T), the electron spin relaxation of Gd(III) dominates the inner-sphere relaxivity, therefore, the strategy of increasing $T_R$ becomes much less efficient to improve r for Gd-based CAs at high fields than low fields. Despite the moderate relaxivity increase, Gd toxicity is likely to persist in these macromolecular CAs[16]. In fact, because most of the conjugation chemistry involves the chelation sites, the Gd affinity will be lowered, contributing to higher risk of heavy metal leakage. In addition, the internal flexibility of these aliphatic dendrimers or polymers also contributed to the less than expected increase in relaxivity per Gd. Lastly, these large CAs are retained in the body for a longer period of time, leading to higher chance of Gd release than small Gd-based CAs.

There is thus a need to create a new generation of CAs that is more efficient and avoids the adverse effects of Gd toxicity. It will be desirable if the new generation of CAs are free of toxic heavy metals such as Gd(III) and exhibit high $T_1$ relaxivity at high field.

SUMMARY

The invention includes a water soluble porphyrin compound of formula (A), or a salt thereof:

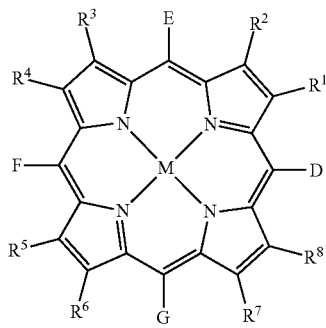

(A)

wherein one or more of D, E and F is defined as in paragraphs (a) to (c):

(a) (i) D is of the formula (LD):

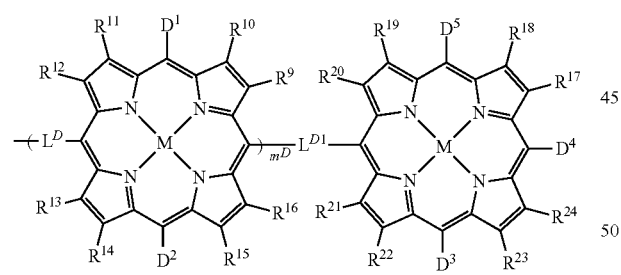

(LD)

wherein:
  each $L^D$ and $L^{D1}$ is independently a covalent bond or a rigid bivalent linker;
  one or the other or both of $D^1$ and $D^2$ is a water-solubilizing group;
  one or more of $D^3$, $D^4$ and $D^5$ is a water-solubilizing group; and
  $m^D$ has a value of from 0 to 20; or (ii) D is of the formula (LD'):

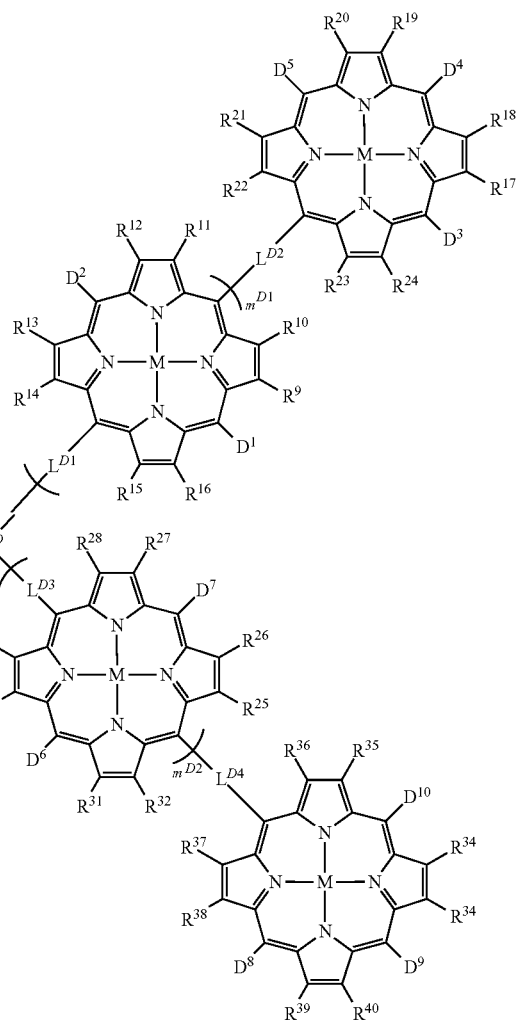

(LD')

wherein:
  $L^D$ is a rigid trivalent linker;
  each $L^{D1}$ is, independently of any other $L^{D1}$, a covalent bond or a rigid bivalent linker;
  each $L^{D2}$ is, independently of any other $L^{D2}$, a covalent bond or a rigid bivalent linker;
  each $L^{D3}$ is, independently of any other $L^{D3}$, a covalent bond or a rigid bivalent linker;
  each $L^{D4}$ is, independently of any other $L^{D4}$, a covalent bond or a rigid bivalent linker:
  one or the other or both of $D^1$ and $D^2$ is a water-solubilizing group;
  one or more of $D^3$, $D^4$ and $D^5$ is a water-solubilizing group;
  one or the other or both of $D^6$ and $D^7$ is a water-solubilizing group;
  one or more of $D^8$, $D^9$ and $D^{10}$ is a water-solubilizing group;
  $m^{D1}$ has a value of from 0 to 20; and
  $m^{D2}$ has a value of from 0 to 20:

(b) (i) E is of the formula (LE):

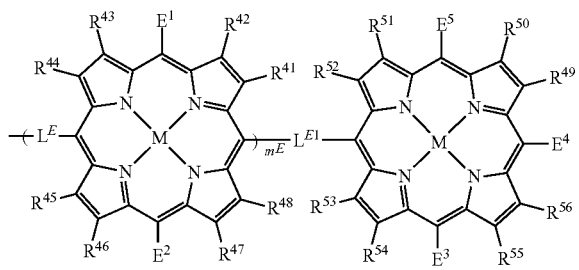

(LE)

wherein:
each $L^E$ and $L^{E1}$ is, independently, a covalent bond or a rigid bivalent linker;
one or the other or both of $E^1$ and $E^2$ is a water-solubilizing group;
one or more of $E^3$, $E^4$ and $E^5$ is a water-solubilizing group;
$m^E$ has a value of from 0 to 20; or (ii) E is of the formula (LE'):

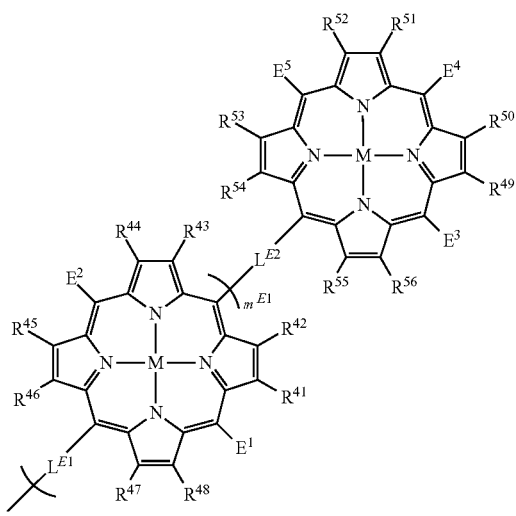

(LE')

-continued

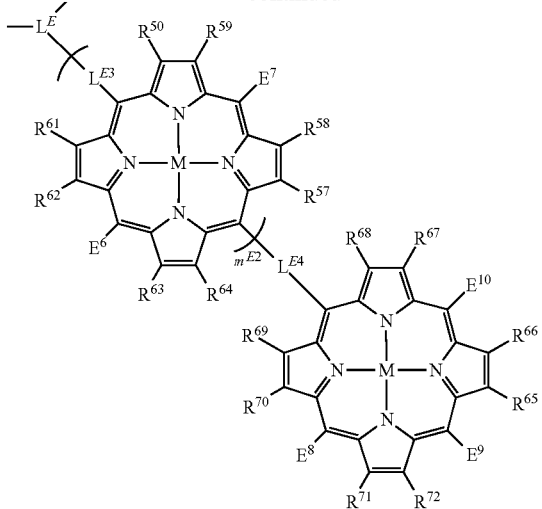

wherein:
$L^E$ is a rigid trivalent linker;
each $L^{E1}$ is, independently of any other $L^{E1}$, a covalent bond or a rigid bivalent linker;
each $L^{E2}$ is, independently of any other $L^{E2}$, a covalent bond or a rigid bivalent linker;
each $L^{E3}$ is, independently of any other $L^{E3}$, a covalent bond or a rigid bivalent linker;
each $L^{E4}$ is, independently of any other $L^{E4}$, a covalent bond or a rigid bivalent linker;
one or the other or both of $E^1$ and $E^2$ is a water-solubilizing group;
one or more of $E^3$, $E^4$ and $E^5$ is a water-solubilizing group;
one or the other or both of $E^6$ and $E^7$ is a water-solubilizing group;
one or more of $E^8$, $E^9$ and $E^{10}$ is a water-solubilizing group;
$m^{E1}$ has a value of from 0 to 20; and
$m^{E2}$ has a value of from 0 to 20;

(c) (i) F is of the formula (LF):

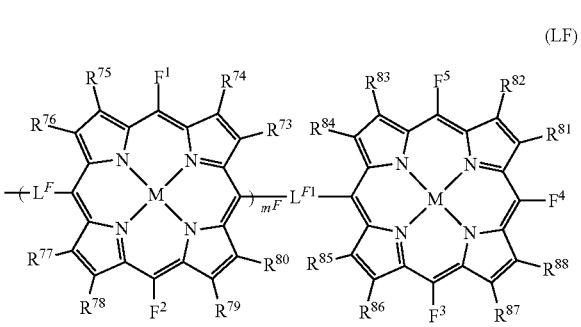

(LF)

wherein:
each $L^F$ and $L^{F1}$ is, independently, a covalent bond or a rigid bivalent linker;
one or the other or both of $F^1$ and $F^2$ is a water-solubilizing group;
one or more of $F^3$, $F^4$ and $F^5$ is a water-solubilizing group;
$L^{F1}$ is a covalent bond or a rigid bivalent linker; and
$m^F$ has a value of from 0 to 20; or (ii) F is of the formula (LF'):

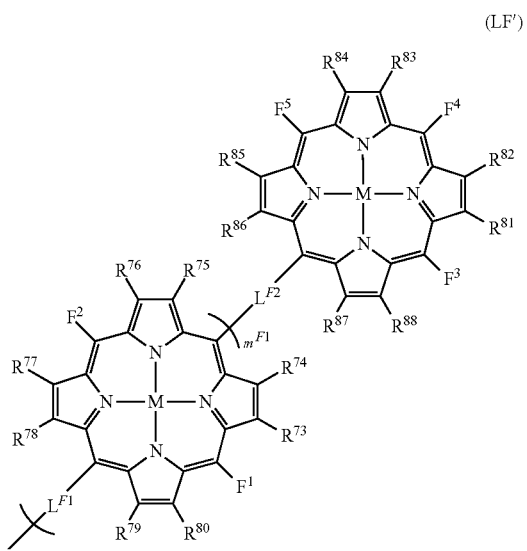

(LF')

wherein:
L$^F$ is a rigid trivalent linker;
each L$^{F1}$ is, independently of any other L$^{F1}$, a covalent bond or a rigid bivalent linker;
each L$^{F2}$ is, independently of any other L$^{F2}$, a covalent bond or a rigid bivalent linker;
each L$^{F3}$ is, independently of any other L$^{F3}$, a covalent bond or a rigid bivalent linker;
each L$^{F4}$ is, independently of any other L$^{F4}$, a covalent bond or a rigid bivalent linker;
one or the other or both of F$^1$ and F$^2$ is a water-solubilizing group;
one or more of F$^3$, F$^4$ and F$^5$ is a water-solubilizing group;
one or the other or both of F$^6$ and F$^7$ is a water-solubilizing group;
one or more of F$^8$, F$^9$ and F$^{10}$ is a water-solubilizing group;
m$^{F1}$ has a value of from 0 to 20; and
m$^{F2}$ has a value of from 0 to 20; and wherein:

when D, E and F are all defined as in paragraphs (a) to (c), G is a water-solubilizing group, or G is defined as in paragraph (d):

(d) (i) G is of the formula (LG):

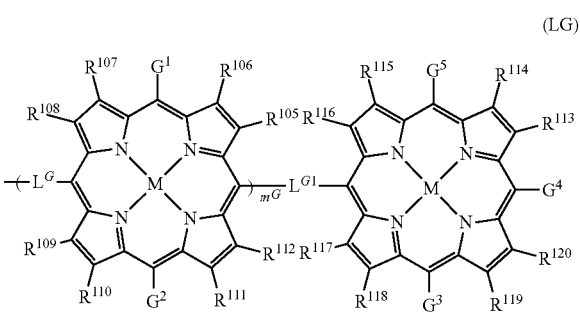

(LG)

wherein:
each L$^G$ and L$^{G1}$ is, independently, a covalent bond or a rigid bivalent liner;
one of the other or both of G$^1$ and G$^2$ is a water-solubilizing group;
one or more of G$^3$, G$^4$ and G$^5$ is a water-solubilizing group;
L$^{G1}$ is a covalent bond or a rigid bivalent linker; and
m$^G$ has a value of from 0 to 20; or (ii) G is of the formula (LG'):

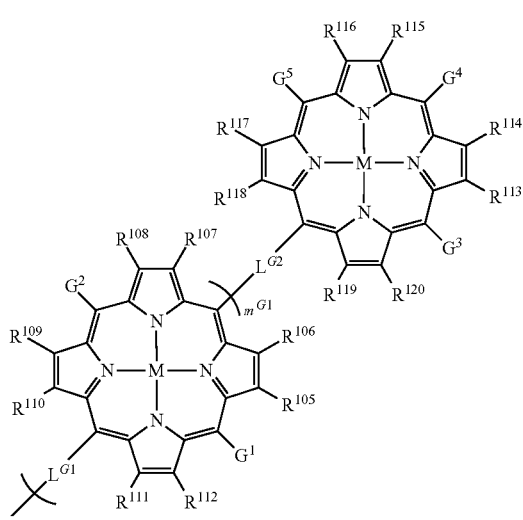

-continued

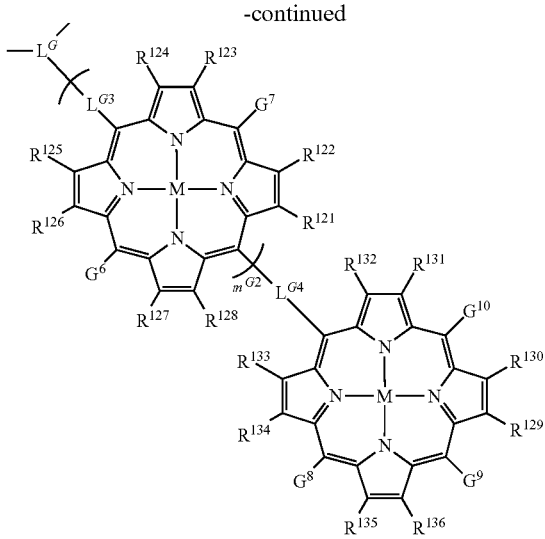

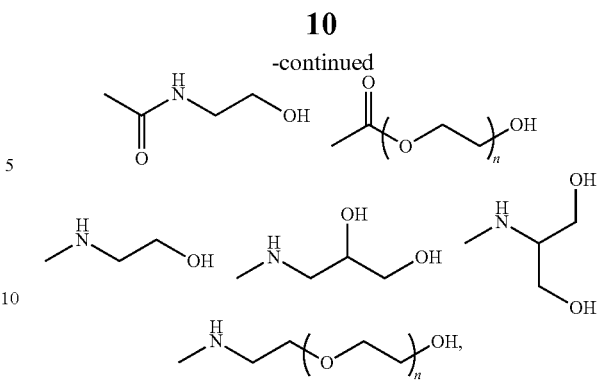

wherein:
- each $L^{G1}$ is, independently of any other $L^{G1}$, a covalent bond or a rigid bivalent linker;
- each $L^{G2}$ is, independently of any other $L^{G2}$, a covalent bond or a rigid bivalent linker;
- each $L^{G3}$ is, independently of any other $L^{G3}$, a covalent bond or a rigid bivalent linker;
- each $L^{G4}$ is, independently of any other $L^{G4}$, a covalent bond or a rigid bivalent linker;
- one or the other or both of $G^1$ and $G^2$ is a water-solubilizing group;
- one or more of $G^3$, $G^4$ and $G^5$ is a water-solubilizing group;
- one or the other or both of $G^6$ and $G^7$ is a water-solubilizing group;
- one or more of $G^8$, $G^9$ and $G^{10}$ is a water-solubilizing group;
- $m^{G1}$ has a value of from 0 to 20; and
- $m^{G2}$ has a value of from 0 to 20; and the sum of $m^D$, $m^{D1}$, $m^{D2}$, $m^E$, $m^{E1}$, $m^{E2}$, $m^F$, $m^{F2}$, $m^G$, $m^{G1}$ and $m^{G2}$ is from 0 to 30; and M is a paramagnetic metal ion present in at least one porphyrin ring, and may be the same or different when present in a plurality of porphyrin rings.

In embodiments of a compound having formula (A), G can be a water-solubilizing group selected from:
(I) carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$, a C$_3$-C$_{20}$ cycloalkyl group containing a nitrogen atom in its ring wherein the cycloalkyl group is bonded to the porphyrin ring by a carbon or nitrogen atom, a C$_3$-C$_{20}$ aryl group containing a nitrogen atom in its ring, and

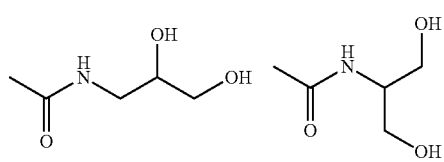

wherein n is from 1 to 20;

C$_1$-C$_{20}$ alkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_3$-C$_{20}$ cycloalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_3$-C$_{20}$ heterocycloalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_1$-C$_{20}$ alkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_3$-C$_{20}$ cycloalkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_3$-C$_{20}$ heterocycloalkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalky (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_6$ to C$_{20}$ aryl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro;

C$_3$ to C$_{20}$ heteroaryl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro;

C$_7$ to C$_{20}$ arylalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_4$ to C$_{20}$ heteroarylalkyl substituted with one or more sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_2$ to C$_{20}$ alkynyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_1$ to C$_{20}$ heteroalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

C$_2$ to C$_{20}$ heteroalkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O); and C$_2$ to C$_{20}$ heteroalkynyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O), wherein each R is independently straight or branched C$_1$-C$_{20}$ alkyl;

In such embodiments, one or more of i.e., at least one of D, E and F can be defined as in foregoing paragraphs (a) to (c) in which:

(A) the one or the other or both of D$^1$ and D$^2$ that is a water-solubilizing group is, independently of the other, as defined in paragraph (1), and the other of D$^1$ and D$^2$ is selected from the group consisting of:

(II) hydrogen;

C$_1$-C$_{20}$ alkyl optionally substituted with up to 4 of any of hydroxyl, halogen, thiol, cyano, nitro, oxo (=O);

C$_3$-C$_{20}$ cycloalkyl optionally substituted with up to 4 of any of hydroxyl, halogen, thiol, cyano, nitro, oxo (=O);

C$_3$-C$_{20}$ heterocycloalkyl optionally substituted with up to 4 of any of hydroxyl, halogen, thiol, cyano, nitro, oxo (=O);

C$_1$-C$_{20}$ alkenyl optionally substituted with up to 4 of any of hydroxyl, halogen, thiol, cyano, nitro, oxo (=O);

C$_3$-C$_{20}$ cycloalkenyl optionally substituted with up to 4 of any of hydroxyl, halogen, thiol, cyano, nitro, oxo (=O);

C$_3$-C$_{20}$ heterocycloalkenyl optionally substituted with up to 4 of any of hydroxyl, halogen, thiol, cyano, nitro, oxo (=O);

C$_6$ to C$_{20}$ aryl optionally substituted with up to 4 of any of hydroxyl, halogen, thiol, cyano, nitro;

C₃ to C₂₀ heteroaryl optionally substituted with up to 4 of any of hydroxyl, halogen, thiol, cyano, nitro;

C₇ to C₂₀ arylalkyl optionally substituted with up to 4 of any of hydroxyl, halogen, thiol, cyano, nitro, oxo (=O);

C₄ to C₂₀ heteroarylalkyl optionally substituted with up to 4 of any of hydroxyl, halogen, thiol, cyano, nitro, oxo (=O);

C₂ to C₂₀ alkynyl optionally substituted with up to 4 of any of hydroxyl, halogen, thiol, cyano, nitro, oxo (=O);

C₁ to C₂₀ heteroalkyl optionally substituted with up to 4 of any of hydroxyl, halogen, thiol, cyano, nitro, oxo (=O);

C₂ to C₂₀ heteroalkenyl optionally substituted with up to 4 of any of hydroxyl, halogen, thiol, cyano, nitro, oxo (=O);

C₂ to C₂₀ heteroalkynyl optionally substituted with up to 4 of any of hydroxyl, halogen, thiol, cyano, nitro, oxo (=O);

(B) the one or more of D³, D⁴ and D⁶ that is a water-solubilizing group is, independently of the others, as defined in paragraph (I), and the other of D³, D⁴ and D⁵ is, independently of the others, as defined in paragraph (II);

(C) the one or the other or both of D⁶ and D⁷ that is a water-solubilizing group is, independently of the other, as defined in paragraph (I), and the other of D⁶ and D⁷ is, independently of the others, as defined in paragraph (II);

(D) the one or the other or both of E¹ and E² that is a water-solubilizing group is, independently of the other, as defined in paragraph (I), and the other of E¹ and E² is, independently of the others, as defined in paragraph (II);

(E) the one or more of E³, E⁴ and E⁵ that is a water-solubilizing group is, independently of the others, as defined in paragraph (I), and the other of E³, E⁴ and E⁵ is, independently of the others, as defined in paragraph (II);

(F) the one or the other or both of E⁶ and E⁷ that is a water-solubilizing group is, independently of the other, as defined in paragraph (I), and the other of E⁶ and E⁷ is, independently of the others, as defined in paragraph (II);

(G) the one or the other or both of F¹ and F² that is a water-solubilizing group is, independently of the other, as defined in paragraph (I), and the other of F¹ and F² is, independently of the others, as defined in paragraph (II);

(H) the one or more of F³, F⁴ and F⁵ that is a water-solubilizing group is, independently of the others, as defined in paragraph (I), and the other of F³, F⁴ and F⁵ is, independently of the others, as defined in paragraph (II);

(I) the one or the other or both of F⁶ and F⁷ that is a water-solubilizing group is, independently of the other, as defined in paragraph (I), and the other of F⁶ and F⁷ is, independently of the others, as defined in paragraph (II); and the other(s) of said one or more of D, E and F can be as defined in paragraph (I) or (II); and each of $R^1$ to $R^{107}$ can be, independently of the others, as defined in paragraph (I) or paragraph (II).

In particular embodiments, each said rigid bivalent linker is, independently, selected from the group consisting of:

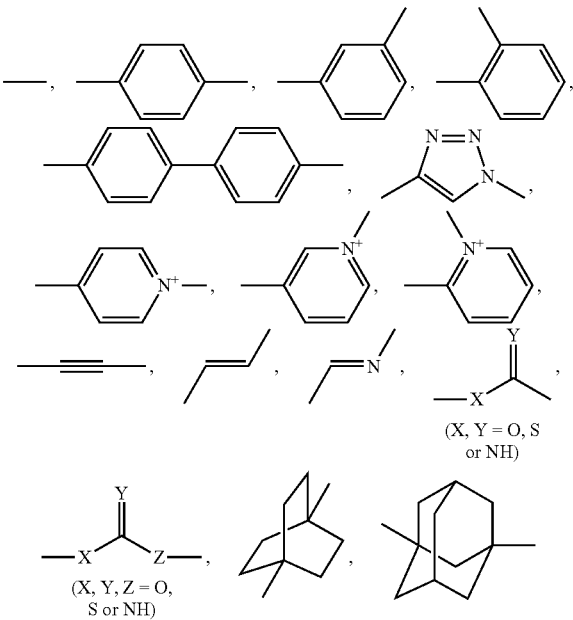

wherein a said linker is optionally substituted with one or more water-solubilising groups and a said linker is optionally substituted with one or more of the substituents defined by paragraph (II). It is preferred that the one or more water-solubilising groups with which such a linker is optionally substituted is selected from the group defined by foregoing paragraph (I).

In such embodiments, each of E and F can be, independently of the other, a water-solubilizing group selected from:

carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), alkylammonium (—NR₃⁺), aminoalkyl (—(C₁-C₂₀ alkyl)NH₂), guanidine (—NHC(NH)NH₂), alkyl guanidine (—NHC(NH)NRH), amido (—C(O)NH₂, a C₃-C₂₀ cycloalkyl group containing a nitrogen atom in its ring wherein the cycloalkyl group is bonded to the porphyrin ring by a carbon or nitrogen atom, a C₃-C₂₀ aryl group containing a nitrogen atom in its ring, and

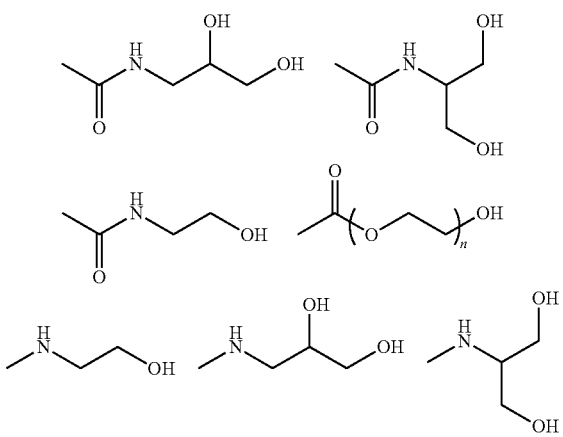

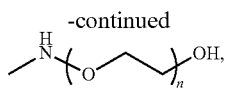

wherein n is from 1 to 20, and each R is independently straight or branched $C_1$-$C_{20}$ alkyl; and D can be of the formula (LD) wherein $m^D$ has a value from 0 to 10.

According to particular embodiments of the compound, or a salt thereof, each $L^D$ and $L^{D1}$ is a covalent bond,

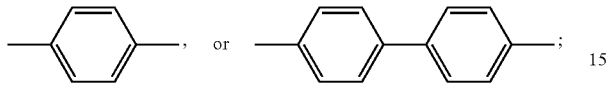

each of $D^1$, $D^2$, $D^3$, $D^4$, $D^5$, E, F and G is p-sulfonated phenyl or carboxyl;
each of $R^1$ to $R^{24}$ is H;
$m^D$ is 8; and
and M is manganese for each porphyrin ring.

In a particular embodiment of the compound, or a salt thereof, D is of the formula (LD);
$m^D=0$;
$L^{D1}$ is:

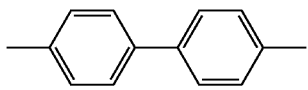

each of D3, D4, D5, E, F and G is p-sulfonated phenyl;
each of $R^1$ to $R^8$ and $R^{17}$ to $R^{24}$ is H; and
each M is manganese.

Other embodiments include a compound, or a salt thereof, wherein D, E, F and G are as defined as in paragraphs (a) to (d) in which:

(aa) the one or the other or both of $D^1$ and $D^2$ that is a water-solubilizing group is, independently of the other, selected from the group consisting of:
(1) carboxyl, sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), alkylammonium (—$NR_3^+$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$, a $C_3$-$C_{20}$ cycloalkyl group containing a nitrogen atom in its ring wherein the cycloalkyl group is bonded to the porphyrin ring by a carbon or nitrogen atom, a $C_3$-$C_{20}$ aryl group containing a nitrogen atom in its ring,

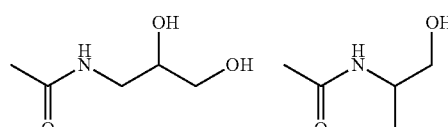
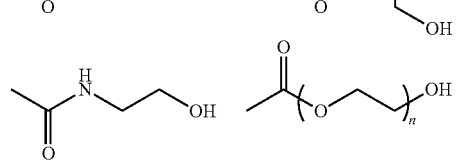

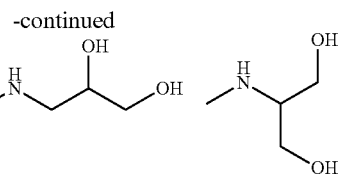
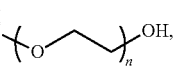

wherein n is from 1 to 20;

$C_1$-$C_{20}$ alkyl substituted with one or more of sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$), and optionally substituted with up to 4 of any of hydroxyl, halogen, thiol, cyano, nitro, oxo (=O);

$C_3$-$C_{20}$ cycloalkyl substituted with one or more of sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$), and optionally substituted with up to 4 of any of hydroxyl, halogen, thiol, cyano, nitro, oxo (=O);

$C_3$-$C_{20}$ heterocycloalkyl substituted with one or more of sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$), and optionally substituted with up to 4 of any of hydroxyl, halogen, thiol, cyano, nitro, oxo (=O);

$C_1$-$C_{20}$ alkenyl substituted with one or more of sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$), and optionally substituted with up to 4 of any of hydroxyl, halogen, thiol, cyano, nitro, oxo (=O);

$C_3$-$C_{20}$ cycloalkenyl substituted with one or more of sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$), alkylphosphinate (—$PO_2R$), amino, alkylamino (—NHR), dialkylamino (—$NR_2$), aminoalkyl (—($C_1$-$C_{20}$ alkyl)$NH_2$), guanidine (—NHC(NH)$NH_2$), alkyl guanidine (—NHC(NH)NRH), amido (—C(O)$NH_2$), and optionally substituted with up to 4 of any of hydroxyl, halogen, thiol, cyano, nitro, oxo (=O);

$C_3$-$C_{20}$ heterocycloalkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

$C_6$ to $C_{20}$ aryl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro;

$C_3$ to $C_{20}$ heteroaryl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro;

$C_7$ to $C_{20}$ arylalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

$C_4$ to $C_{20}$ heteroarylalkyl substituted with one or more sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

$C_2$ to $C_{20}$ alkynyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

$C_1$ to $C_{20}$ heteroalkyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O);

$C_2$ to $C_{20}$ heteroalkenyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O); and $C_2$ to $C_{20}$ heteroalkynyl substituted with one or more of sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$), and optionally substituted with up to 4 of any of hydroxyl, halogen, thiol, cyano, nitro, oxo (=O), wherein each R is independently straight or branched $C_1$-$C_{20}$ alkyl;

(bb) the other of $D^1$ and $D^2$ is selected from the group consisting of:

(2) hydrogen;

$C_1$-$C_{20}$ alkyl optionally substituted with up to 4 of any of hydroxyl, halogen, thiol, cyano, nitro, oxo (=O);

$C_3$-$C_{20}$ cycloalkyl optionally substituted with up to 4 of any of hydroxyl, halogen, thiol, cyano, nitro, oxo (=O);

$C_3$-$C_{20}$ heterocycloalkyl optionally substituted with up to 4 of any of hydroxyl, halogen, thiol, cyano, nitro, oxo (=O);

$C_1$-$C_{20}$ alkenyl optionally substituted with up to 4 of any of hydroxyl, halogen, thiol, cyano, nitro, oxo (=O);

$C_3$-$C_{20}$ cycloalkenyl optionally substituted with up to 4 of any of hydroxyl, halogen, thiol, cyano, nitro, oxo (=O);

$C_3$-$C_{20}$ heterocycloalkenyl optionally substituted with up to 4 of any of hydroxyl, halogen, thiol, cyano, nitro, oxo (=O);

$C_6$ to $C_{20}$ aryl optionally substituted with up to 4 of any of hydroxyl, halogen, thiol, cyano, nitro;

$C_3$ to $C_{20}$ heteroaryl optionally substituted with up to 4 of any of hydroxyl, halogen, thiol, cyano, nitro;

$C_7$ to $C_{20}$ arylalkyl optionally substituted with up to 4 of any of hydroxyl, halogen, thiol, cyano, nitro, oxo (=O);

$C_4$ to $C_{20}$ heteroarylalkyl optionally substituted with up to 4 of any of hydroxyl, halogen, thiol, cyano, nitro, oxo (=O);

C$_2$ to C$_{20}$ alkynyl optionally substituted with up to 4 of any of hydroxyl, halogen, thiol, cyano, nitro, oxo (=O);

C$_1$ to C$_{20}$ heteroalkyl optionally substituted with up to 4 of any of hydroxyl, halogen, thiol, cyano, nitro, oxo (=O);

C$_2$ to C$_{20}$ heteroalkenyl optionally substituted with up to 4 of any of hydroxyl, halogen, thiol, cyano, nitro, oxo (=O);

C$_2$ to C$_{20}$ heteroalkynyl optionally substituted with up to 4 of any of hydroxyl, halogen, thiol, cyano, nitro, oxo (=O);

(cc) the one or more of D$^3$, D$^4$ and D$^5$ that is a water-solubilizing group is, independently of the others, as defined in paragraph (1), and the other of D$^3$, D$^4$ and D$^5$ is, independently of the others, as defined in paragraph (2);

(dd) the one or the other or both of D$^6$ and D$^7$ that is a water-solubilizing group is, independently of the other, as defined in paragraph (1), and the other of D$^6$ and D$^7$ is, independently of the others, as defined in paragraph (2);

(ee) the one or the other or both of E$^1$ and E$^2$ that is a water-solubilizing group is, independently of the other, as defined in paragraph (1), and the other of E$^1$ and E$^2$ is, independently of the others, as defined in paragraph (2);

(ff) the one or more of E$^3$, E$^4$ and E$^5$ that is a water-solubilizing group is, independently of the others, as defined in paragraph (1), and the other of E$^3$, E$^4$ and E$^5$ is, independently of the others, as defined in paragraph (2);

(gg) the one or the other or both of E$^6$ and E$^7$ that is a water-solubilizing group is, independently of the other, as defined in paragraph (1), and the other of E$^6$ and E$^7$ is, independently of the others, as defined in paragraph (2);

(hh) the one or the other or both of F$^1$ and F$^2$ that is a water-solubilizing group is, independently of the other, as defined in paragraph (1), and the other of F$^1$ and F$^2$ is, independently of the others, as defined in paragraph (2);

(ii) the one or more of F$^3$, F$^4$ and F$^5$ that is a water-solubilizing group is, independently of the others, as defined in paragraph (1), and the other of F$^3$, F$^4$ and F$^5$ is, independently of the others, as defined in paragraph (2);

(jj) the one or the other or both of F$^6$ and F$^7$ that is a water-solubilizing group is, independently of the other, as defined in paragraph (1), and the other of F$^6$ and F$^7$ is, independently of the others, as defined in paragraph (2);

(kk) the one or the other or both of G$^1$ and G$^2$ that is a water-solubilizing group is, independently of the other, as defined in paragraph (1), and the other of G$^1$ and G$^2$ is, independently of the others, as defined in paragraph (2);

(ll) the one or more of G$^3$, G$^4$ and G$^5$ that is a water-solubilizing group is, independently of the others, as defined in paragraph (1), and the other of G$^3$, G$^4$ and G$^5$ is, independently of the others, as defined in paragraph (2); and (mm) the one or the other or both of G$^6$ and G$^7$ that is a water-solubilizing group is, independently of the other, as defined in paragraph (1), and the other of G$^6$ and G$^7$ is, independently of the others, as defined in paragraph (2), and each of R$^1$ to R$^{136}$ is, independently of the others, as defined in paragraph (1) or paragraph (2).

Preferred aspects of such embodiments are compounds or their salts, in which:

D is of the formula (LD'), E is of the formula (LE'), F is of the formula (LF'), G is of the formula (LG');

$m^{D1}=m^{D2}=m^{E1}=m^{E2}=m^{F1}=m^{F2}=m^{G1}=m^{G2}=0;$ each of L$^{D2}$, L$^{D4}$, L$^{E2}$, L$^{E4}$, L$^{F2}$ L$^{F4}$, L$^{G2}$ and L$^{G4}$ is a covalent bond,

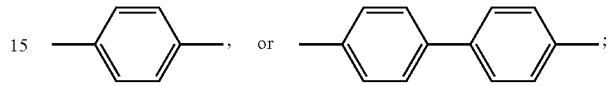

and each of D$^3$, D$^4$, D$^5$, D$^8$, D$^9$, D$^{10}$, E$^3$, E$^4$, E$^5$, E$^8$, E$^9$, E$^{10}$, F$^3$, F$^4$, F$^5$, F$^8$, F$^9$, F$^{10}$, G$^3$, G$^4$, G$^5$, G$^8$, G$^9$ and G$^{10}$ is p-sulfonated phenyl or carboxyl.

In a preferred aspect of the compound, or a salt thereof, each of L$^D$, L$^E$, L$^F$ and L$^G$ is:

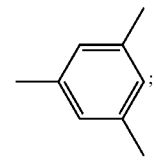

each of L$^{D2}$, L$^{D4}$, L$^{E2}$, L$^{E4}$, L$^{F2}$ L$^{F4}$, L$^{G2}$ and L$^{G4}$ is

each of D$^3$, D$^4$, D$^5$, D$^8$, D$^9$, D$^{10}$, E$^3$, E$^4$, E$^5$, E$^8$, E$^9$, E$^{10}$, F$^3$, F$^4$, F$^5$, F$^8$, F$^9$, F$^{10}$, G$^3$, G$^4$, G$^5$, G$^8$, G$^9$ and G$^{10}$ is p-sulfonated phenyl;

each of R$^1$ to R$^8$, R$^{17}$ to R$^{24}$, R$^{33}$ to R$^{40}$, R$^{49}$ to R$^{56}$, R$^{65}$ to R$^{72}$, R$^{113}$ to R$^{120}$ and R$^{129}$ to R$^{136}$ is H; and each M is manganese.

A second broad aspect of the invention is a water soluble porphyrin compound of formula (A), or a salt thereof:

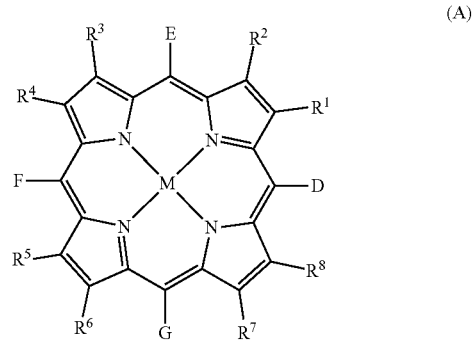

(A)

wherein:
each of $R^1$ to $R^8$ and D, E, F and G is independently selected from the group consisting of:

hydrogen, halogen, thiol, cyano, nitro, amido (—C(O)NH$_2$), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$, a C$_3$-C$_{20}$ cycloalkyl group containing a nitrogen atom in its ring wherein the cycloalkyl group is bonded to the porphyrin ring by a carbon or nitrogen atom, a C$_3$-C$_{20}$ aryl group containing a nitrogen atom in its ring, and

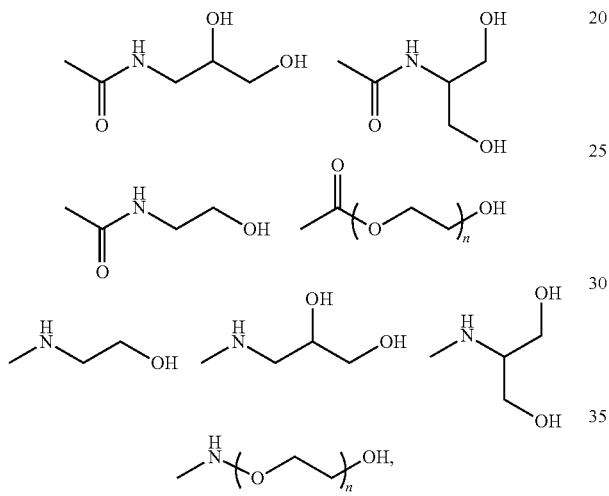

wherein n is from 1 to 20;

C$_1$-C$_{20}$ alkyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_3$-C$_{20}$ cycloalkyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_3$-C$_{20}$ heterocycloalkyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_1$-C$_{20}$ alkenyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_3$-C$_{20}$ cycloalkenyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_3$-C$_{20}$ heterocycloalkenyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_6$ to C$_{20}$ aryl, optionally substituted with up to 4 of any of hydroxyl, halogen, thiol, cyano, nitro, carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_3$ to C$_{20}$ heteroaryl, optionally substituted with up to 4 of any of hydroxyl, halogen, thiol, cyano, nitro, carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_7$ to C$_{20}$ arylalkyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_{20}$ alkyl)NH$_2$), guanidine (—NHC(NH)NH$_2$), alkyl guanidine (—NHC(NH)NRH), amido (—C(O)NH$_2$);

C$_4$ to C$_{20}$ heteroarylalkyl, optionally substituted with up to 4 of any of hydroxyl, halogen, thiol, cyano, nitro, oxo (=O), carboxyl, sulfonate, phosphate (—OPO$_3$H$_2$), alkylphosphate (—OPO$_3$RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂);

C₂ to C₂₀ alkynyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—P₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂);

C₁ to C₂₀ heteroalkyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂);

C₂ to C₂₀ heteroalkenyl, optionally substituted with up to 4 of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂); and C₂ to C₂₀ heteroalkynyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂), wherein each R is independently straight or branched C₁-C₂₀ alkyl, wherein at least one of R¹ to R⁸ and D, E, F and G is carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH).

12. A compound as claimed in claim 11, or a salt thereof, wherein:

each of D, E, F and G is selected from the group consisting of:

carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), alkylammonium (—NR₃⁺), guanidine (—NHC(NH)NH₂), alkyl guanidine (—NHC(NH)NRH), and

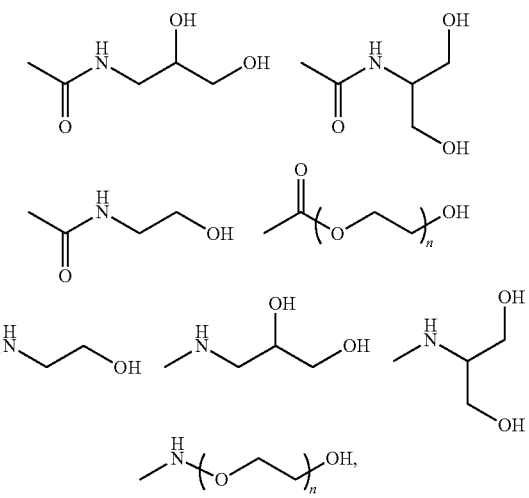

In preferred aspects, each of D, E, F and G is carboxyl, each of R¹ to R⁸ is hydrogen; and M is manganese.

Compounds and salts find use as CAs in MRI. In an aspect, the invention includes a pharmaceutical formulation containing a compound or salt thereof, as described herein. Such a formulation includes a pharmaceutically acceptable carrier, wherein the formulation is suitable for administration as an imaging enhancing agent and the contrast agent is present in an amount sufficient to enhance a magnetic resonance image.

According to another aspect, the invention is a method of generating an image of at least a part of a subject. The method includes administering a compound or salt thereof, as described herein, to a subject, and generating an image of at least a part of said subject to which said compound has been distributed.

According to an embodiment, the invention includes a method of imaging a tumor and surrounding tissue in a subject comprising administering to the subject a composition comprising a compound or salt thereof, as described herein, and imaging the tumor and surrounding tissue in said subject.

The invention includes a composition containing a compound or salt thereof, as described herein, and a pharmaceutically acceptable carrier, excipient or diluent, suitable for administration to a subject.

The invention is also a method for imaging a patient. The method includes administering a composition comprising a compound or salt thereof, as described herein, as a blood-pool imaging agent, and obtaining a magnetic resonance angiography (MRA).

BRIEF DESCRIPTION OF DRAWINGS

Embodiments will now be described, by way of example only, reference being made to the accompanying drawings, in which.

DETAILED DESCRIPTION

Figure 1:
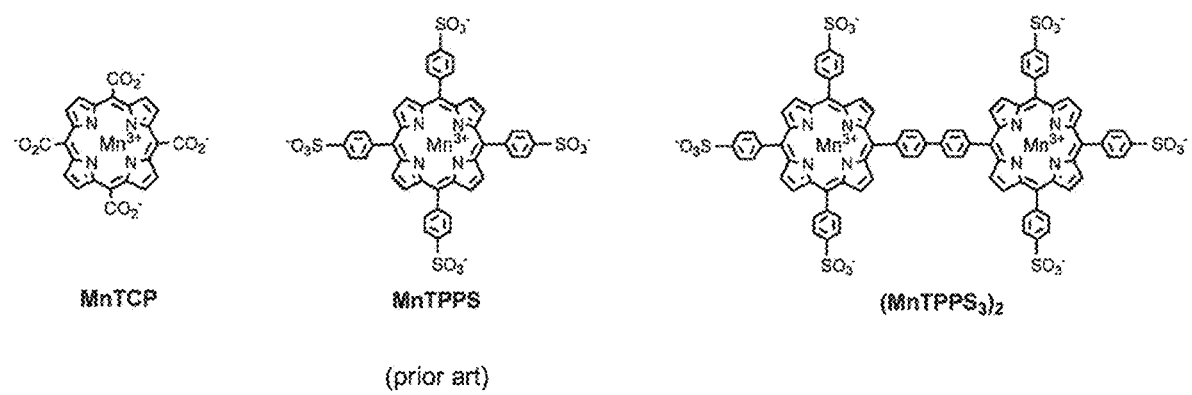
FIG. 1 shows chemical structures of MnTCP, MnTPPS (prior art) and $(MnTPPS_3)_2$.

An embodiment of the invention is represented by a porphyrin compound of formula (A), exemplified here by MnTCP:

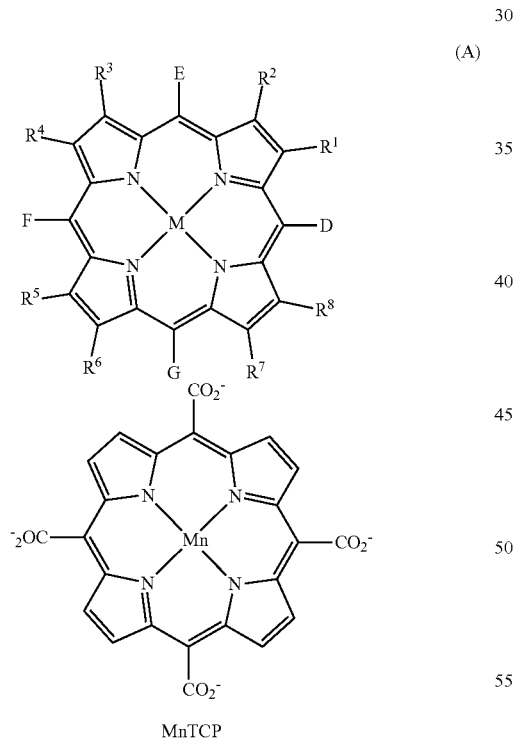

(A)

MnTCP

In MnTCP, each of $R^1$ to $R^8$ of a compound of formula (A) is a hydrogen atom, and each of D, E, F and G is a carboxyl group, shown in the ionized form for convenience, and the metal complexed by the porphyrin ring is manganese, which is Mn(III) in the exemplified embodiment, described below.

Another embodiment of the invention is represented by a porphyrin compound of formula (A-LD) exemplified by $(MnTPPS_3)_2$:

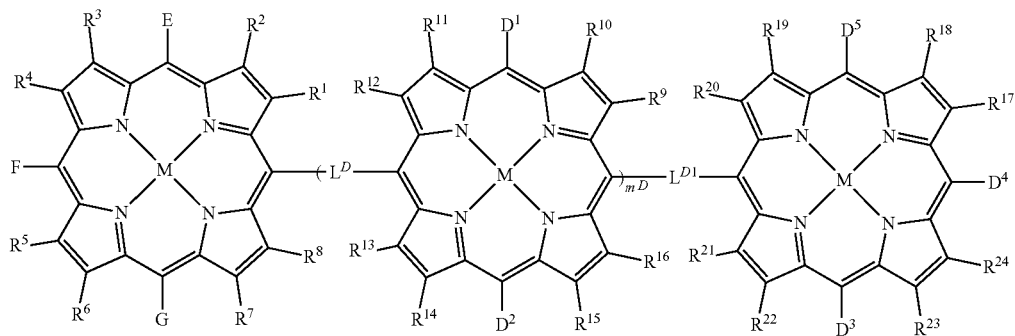

A-LD

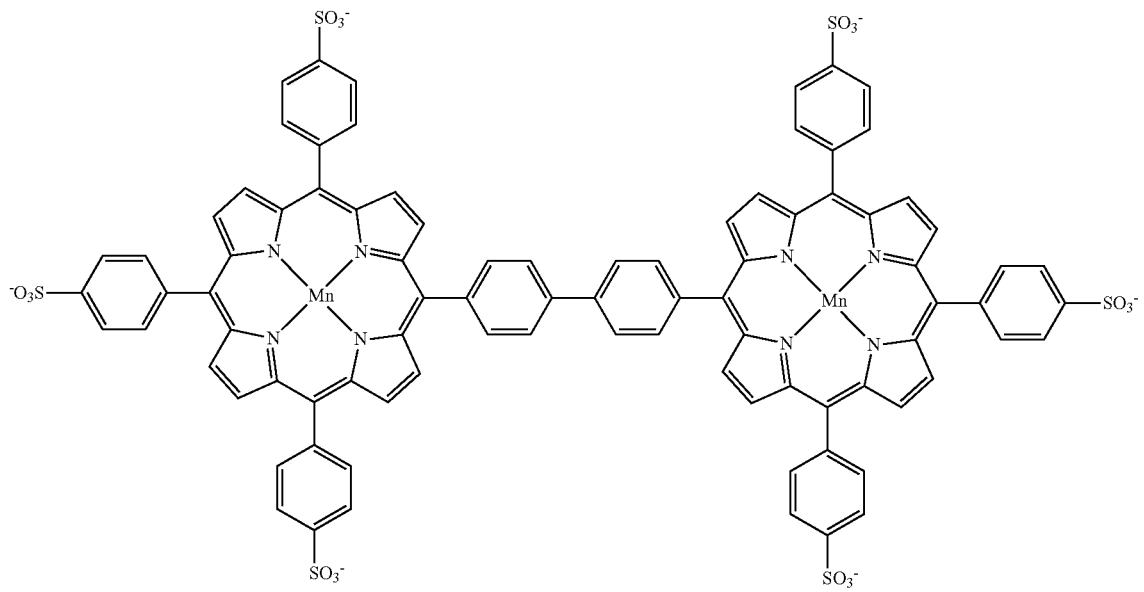

(MnTPPS₃)₂

In (MnTPPS₃)₂, substituent D of compound A is LD in which $m^D=0$ and $L^{D1}$ is a biphenyl group in which each phenyl group is para-substituted, each of $R^1$ to $R^8$ and $R^{17}$ to $R^{24}$ is a hydrogen atom, and each of $D^3$, $D^4$, $D^5$, E, F and G is a para-sulfonated phenyl group, shown in the ionized form for convenience, and the metal complexed by each porphyrin ring is manganese, which is Mn(III) in the exemplified embodiment, described below.

Embodiments of the invention include compounds of formula (A) similar to (MnTPPS₃)₂ in which aromatic rings of the linkers bear solubilising groups, such as sulfonate groups:

29
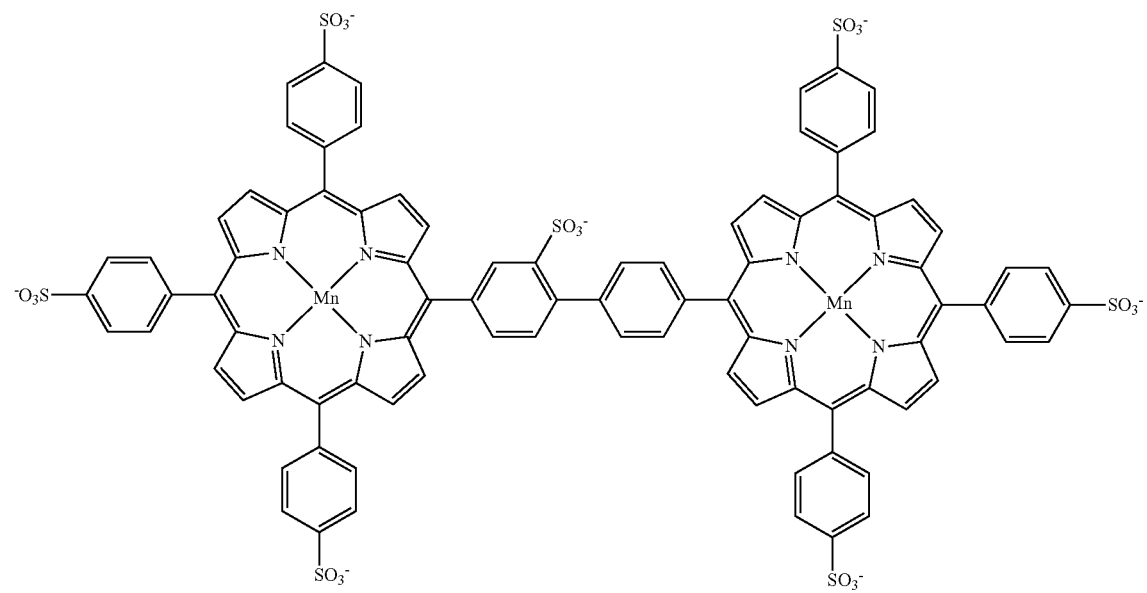
30
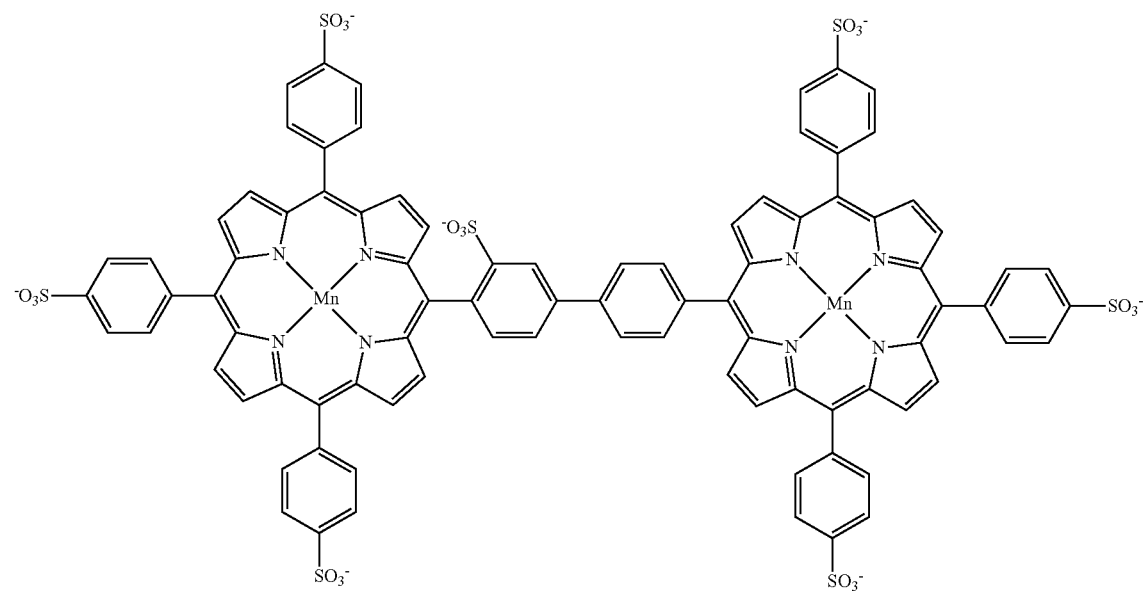

-continued

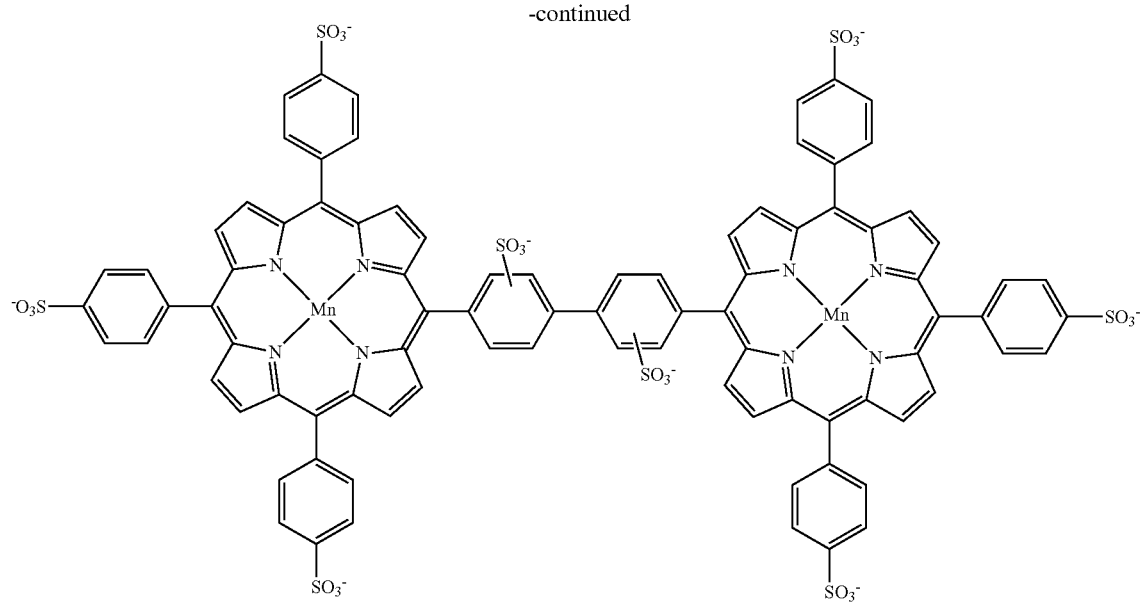

Another polyporphyrin related to (MnTPPS$_3$)$_2$, is one in which substituent D of compound A is LD and L$^D$ and L$^{D1}$ are biphenyl groups, m$^D$ is from 1 to 30, each of R$^1$ to R$^{24}$ is a hydrogen atom, and each of D$^1$, D$^2$, D$^3$, D$^4$, D$^5$, E, F and G is a para-sulfonated phenyl group:

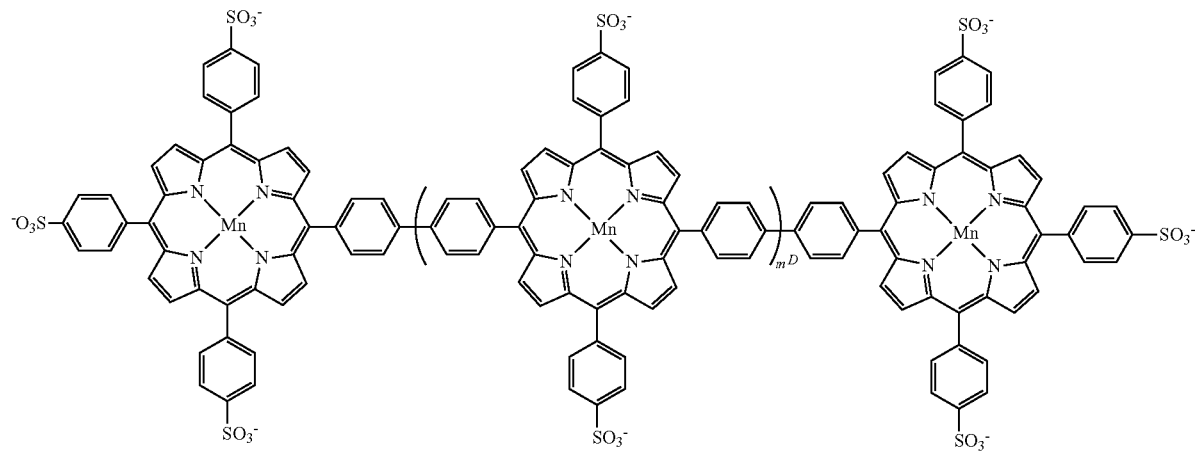

An embodiment of the invention is a compound of formula (A) in which substituent D is LD and m$^D$=0 and L$^{D1}$ is a phenyl group linking porphyrin rings by through covalent bonds at para-positions, each of R$^1$ to R$^{24}$ is a hydrogen atom, and each of D$^3$, D$^4$, D$^5$, E, F and G is a para-sulfonated phenyl group, shown in the ionized form for convenience, and the metal complexed by each porphyrin ring is manganese, which is Mn(III):

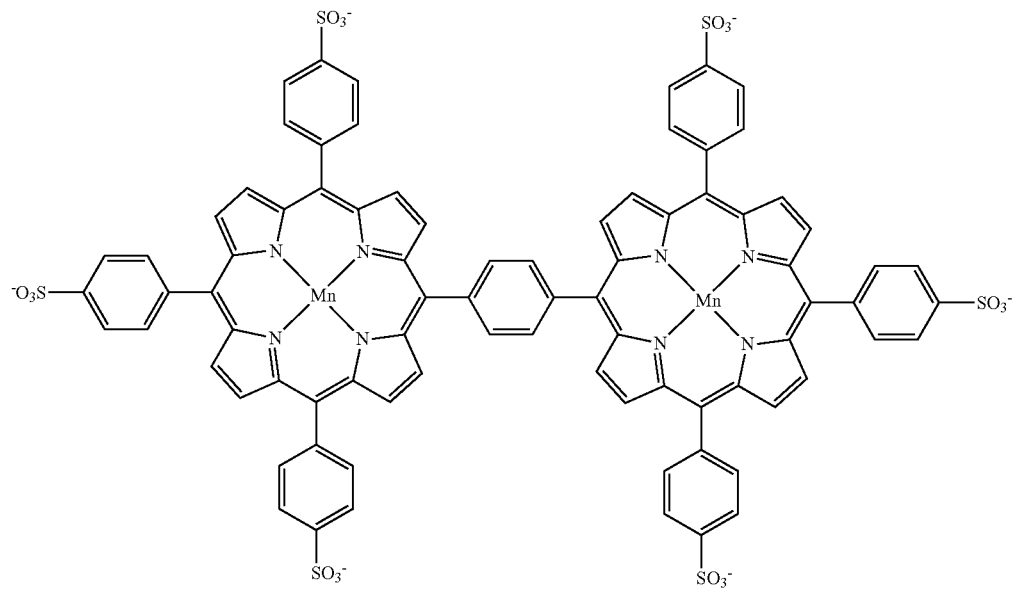
Another embodiment of the invention is a compound of formula (A) in which substituent D is LD and $m^D=0$ and $L^{D1}$ is a covalent bond, each of $R^1$ to $R^{24}$ is a hydrogen atom, and each of $D^3$, $D^4$, $D^5$, E, F and G is a para-sulfonated phenyl group, shown in the ionized form for convenience, and the metal complexed by each porphyrin ring is manganese, which is Mn(III):
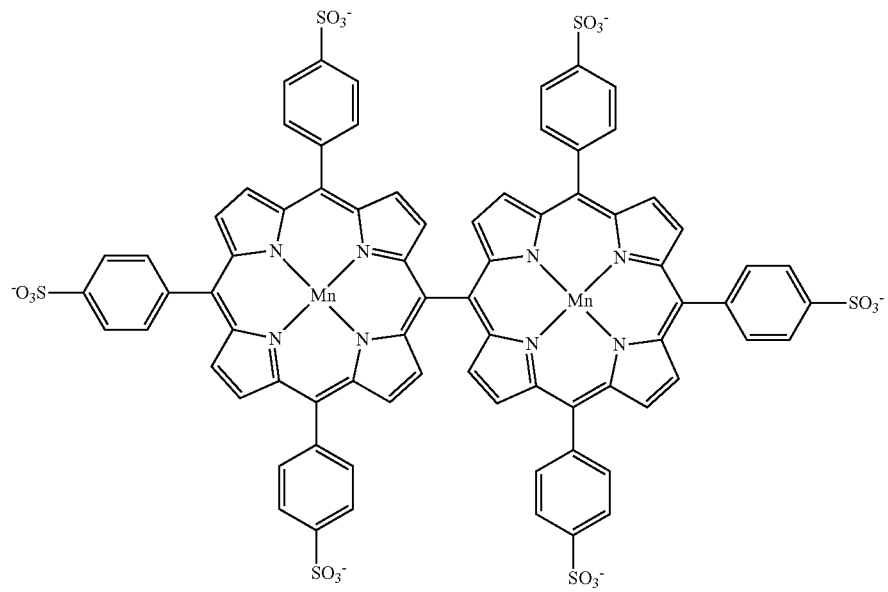

Another embodiment of the invention is (MnTCP)$_2$:

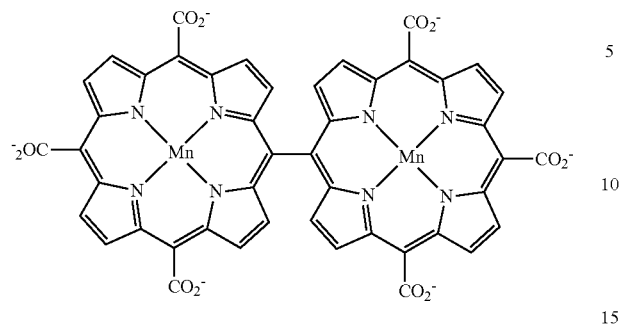

(MnTCP)$_2$ is thus a compound of formula (A) in which substituent D is LD and $m_D=0$ and $L^{D1}$ is a covalent bond linking meso-positions of porphyrin rings, each of $R^1$ to $R^7$ and $R^{17}$ to $R^{24}$ is a hydrogen atom, and each of $D^3$, $D^4$, $D^5$, E, F and G is a carboxyl group, shown above in the ionized form for convenience, and the metal complexed by each porphyrin ring is manganese.

A related polyporphyrin is one in which substituent D of compound A is LD and $L_D$ and $L^{D1}$ are covalent linkages between meso-positions of porphyrin rings, $m^D$ is from 1 to 30, each of $R^1$ to $R^{24}$ is a hydrogen atom, and each of $D^1$, $D^2$, $D^3$, $D^4$, $D^5$, E, F and G is a carboxyl group:

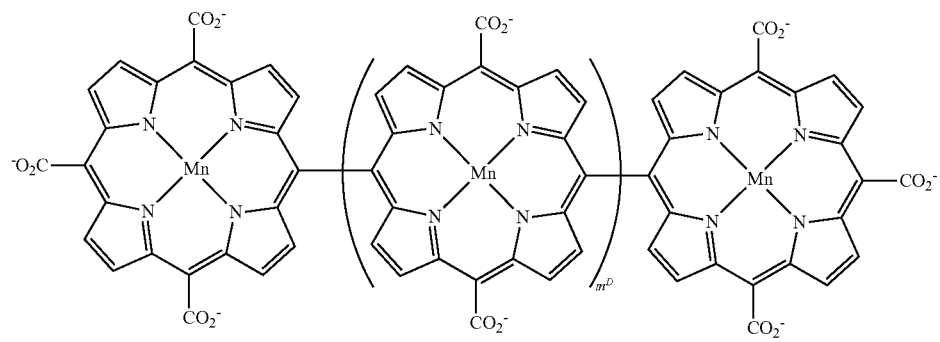

Embodiments of the invention include polyporphyrins in which each of D, E, F and G includes a porphyrin ring. In one such embodiment, D, E, F and G are LD, LE, LF, and LG, respectively in which $m^D$, $m^E$, $m^F$ and $m^G$ are all equal to zero; each of $D^3$, $D^4$, $D^5$, $E^3$, $E^4$, $E^5$, $F^3$, $F^4$, $F^5$, $G^3$, $G^4$ and $G^5$ is a para-sulfonated phenyl group; each of $L^{D1}$, $L^{E1}$, $L^{F1}$ and $L^{G1}$ is a biphenyl group; and all β-positions of the porphyrin rings are unsubstituted i.e., $R^1$ to $R^8$, $R^{17}$ to $R^{24}$, $R^{49}$ to $R^{56}$, $R^{81}$ to $R^{88}$, and $R^{113}$ to $R^{120}$ are all hydrogen atoms:

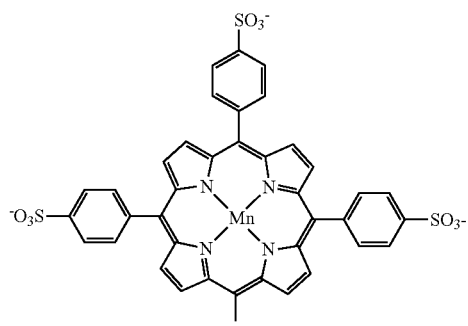

-continued

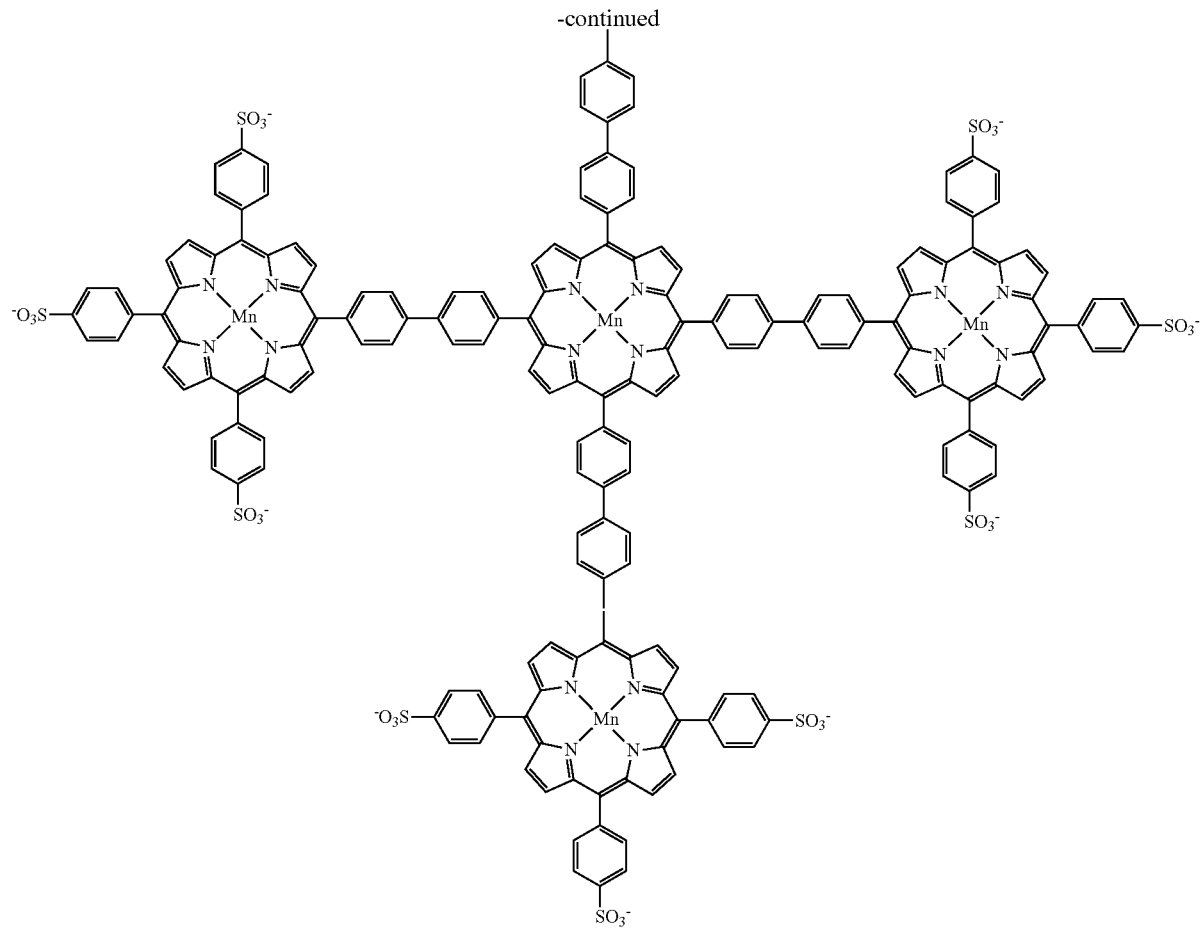

In another such embodiment, in which each of D, E, F and G includes a porphyrin ring, D, E, F and G are LD', L', LF' and LG' wherein $m^{D1}$, $m^{D2}$, $m^{E1}$, $m^{E2}$ $m^{F1}$, $m^{F2}$, $m^{G1}$ and $m^{G2}$ are all equal to zero; each of $D^3$, $D^4$, $D^5$, $D^8$, $D^9$, $D^{10}$, $E^3$, $E^4$, $E^5$, $E^8$, $E^9$, $E^{10}$, $F^3$, $F^4$, $F^5$, $F^8$, $F^9$, $F^{10}$, $G^3$, $G^4$, $G^5$, $G^8$, $G^9$ and $G^{10}$ is a para-sulfonated phenyl group; and all β-positions of the porphyrin rings are unsubstituted i.e., $R^1$ to $R^8$, $R^{17}$ to $R^{24}$, $R^{33}$ to $R^{40}$, $R^{49}$ to $R^{56}$, $R^{65}$ to $R^{72}$, $R^{81}$ to $R^{88}$, $R^{97}$ to $R^{104}$, $R^{113}$ to $R^{120}$ and $R^{129}$ to $R^{136}$ are all hydrogen atoms:

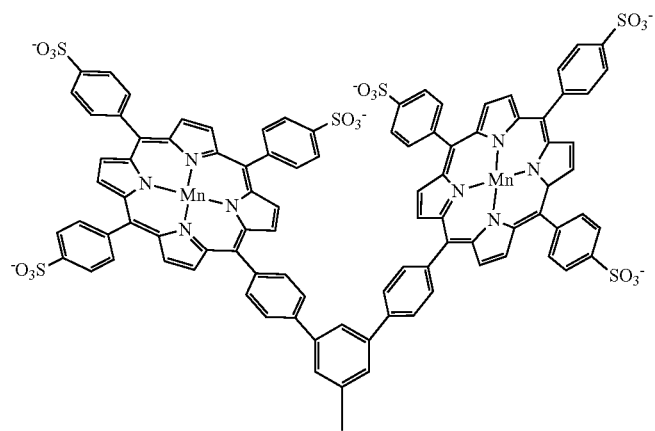

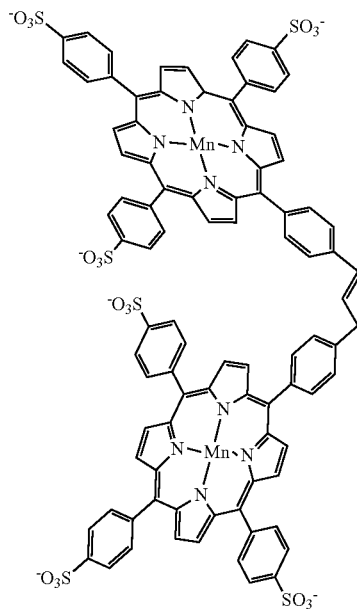
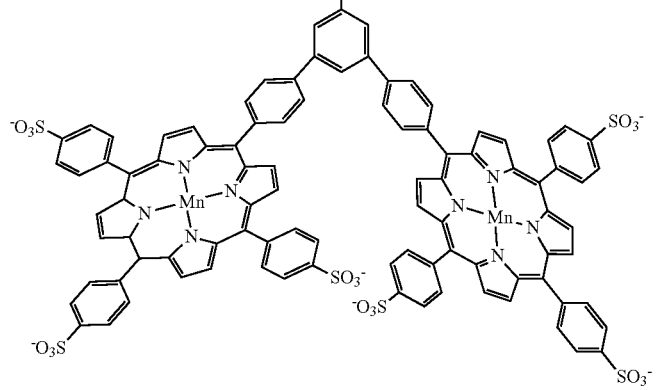
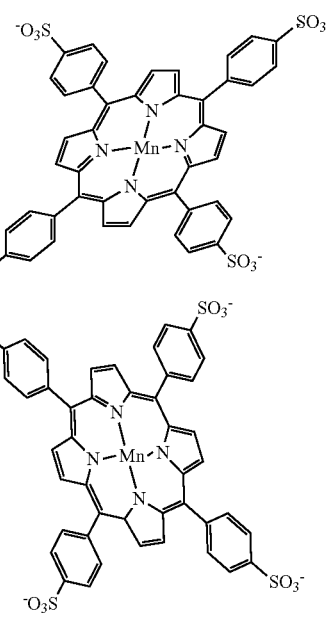

One can thus see that disclosed embodiments encompass monomeric, dimeric and oligomeric porphyrins. In preferred embodiments, the molecules are free of gadolinium, and M can be manganese, either Mn(II) or Mn(III), preferably Mn(III). Useful as contrast agents, compounds of the invention include substituent groups that render the compound soluble in water i.e., a biological medium provided by the human body in the context of clinical examinations, particularly, plasma, blood and biological fluids.

Field-dependent $T_1$ relaxivities of MnTCP and (MnTPPS$_3$)$_2$ were examined and compared to known agents, MnTPPS and Gd-DTPA. Chen et al. first reported the relaxivity of MnTPPS at ~0.5 T (20 MHz)[17], and Konieg and colleagues subsequently measured the $T_1$ Nuclear Magnetic Resonance Dispersion (NMRD) profile (field-dependent relaxivity) of this monomeric MnP[18] and found that it exhibits "anomalous high relaxivity", considering there are only four unpaired electrons (S=4/2) in Mn(III) relative to seven in Gd(III).

The relaxivity of MnTPPS peaks at 0.2 T at 37° C. and plateaus at >10 mM$^{-1}$ s$^{-1}$ up to 1 T.[18] The rigidity of the porphyrin scaffold reduces internal rotation and efficiently lowers the rotational diffusion rate of the CAs. The electron configuration of the complex is important to determining relaxivity. Since porphyrins have large conjugated π systems, electronic properties at the paramagnetic center can be tuned by introducing different functional groups on the porphyrin ring. Structural modifications made available by approaches described herein, such as appending polar groups to the porphyrin ring can not only optimize the electronic properties but also be made to tune the CA's pharmacokinetics. Small and polar porphyrins can be used as extracellular fluid CAs since they tend to be cleared rapidly by the kidney. Large porphyrins that have relatively high relaxivity and longer retention times in the body can be used for targeted imaging. Porphyrin chelates can have extended applications such as PET imaging (replacing Mn(III) with a radioactive isotope $^{51}$Mn. Moreover, fluorescence imaging and photodynamic therapy (PDT) can be performed if diamagnetic versions, such as metal-free or Zn(II)-inserted porphyrins are used[19].

Figure 2:
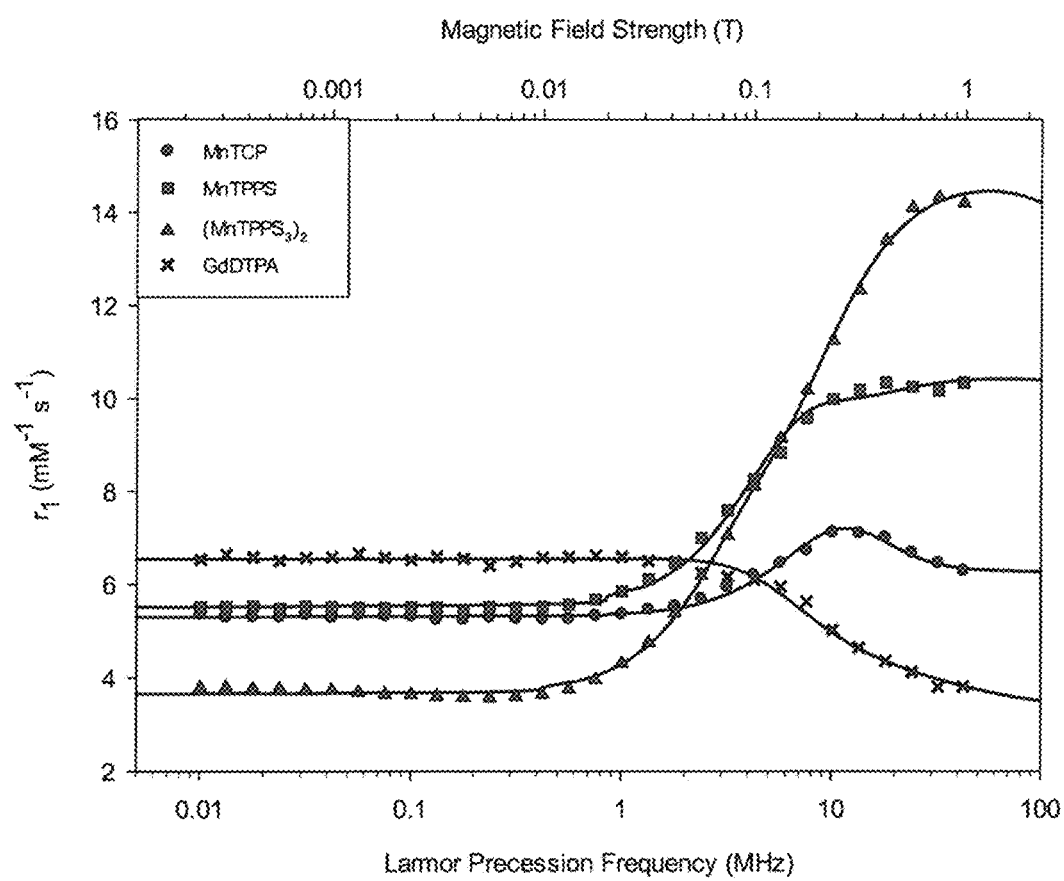
FIG. 2 shows NMRD of, in ascending order along the left-hand side of the plots, $(MnTPPS_3)_2$, MnTCP, MnTPPS (prior art), and Gd-DTPA (prior art). $T_1$ relaxivity values were measured per Mn(III) or Gd(III) up to 1 T.

NMRD profiles were obtained to demonstrate continuous field-dependent $T_1$ relaxivities. These were recorded using a field cycling NMR relaxometer covering magnetic fields from 0 to 1 T. As shown in FIG. 2, compared to MnTPPS, MnTCP, and Gd-DTPA, the dimeric (MnTPPS$_3$)$_2$ exhibited the highest relaxivity per Mn at fields above ~0.2 T. The relaxivity peak of $(MnTPPS_3)_2$ occurs close to 1 T and this broad peak extends to higher fields of 3 T and above, favoring high relaxivity at high magnetic fields. Although MnTCP displayed a lower relaxivity than MnTPPS at clinical field strengths, it was still found to be substantially higher than Gd-DTPA at fields above 0.2 T.

Figure 3:
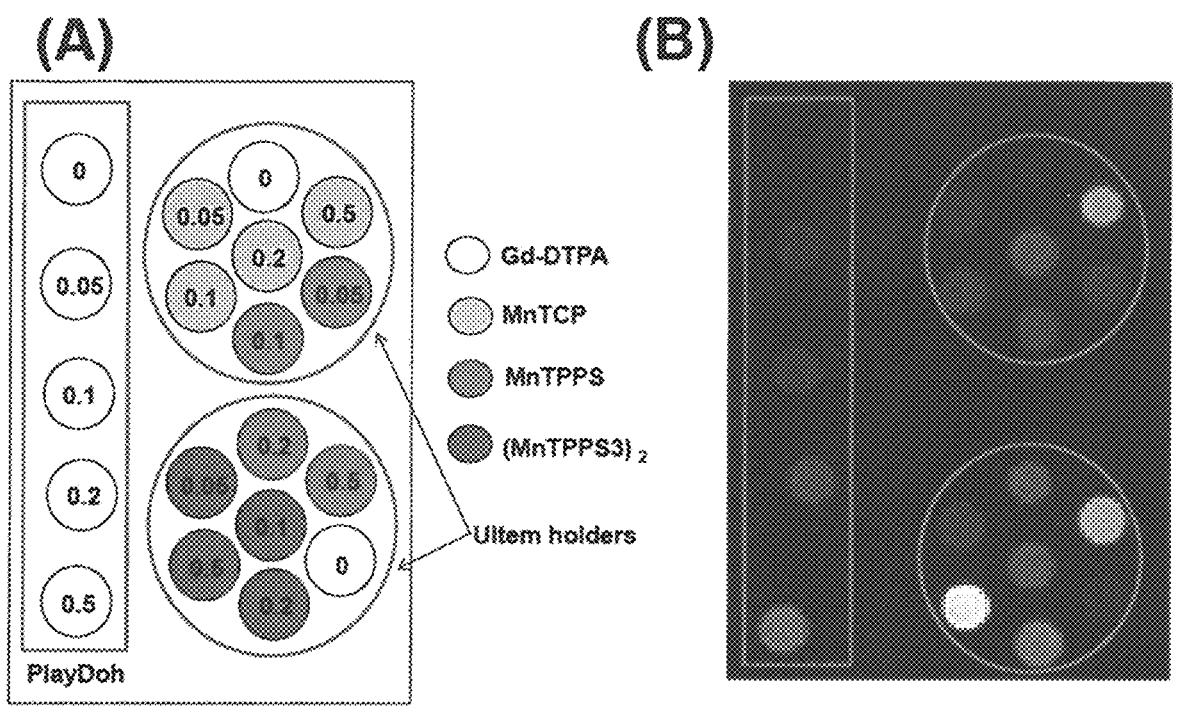
FIG. 3 shows $T_1$ weighted spin echo phantom images (TR=122 ms, TE=18.5 ms) of Gd-DTPA, MnTCP, MnTPPS and $(MnTPPS_3)_2$ at 3 T and 25° C. (A) A schematic diagram of how the solutions are placed. (B) The corresponding phantom images produced by the 3 T scanner.

Relaxivities of MnPs at 3 T were measured on a clinical MRI scanner (Philips Achieva). Each of the four CAs were prepared in a series of increasing concentrations, 0, 0.05, 0.1, 0.2 and 0.5 mM, and imaged using an inversion-recovery spin-echo pulse sequence with varied inversion times TI and a multi-echo spin-echo sequence with varied echo times TE. As demonstrated in FIG. 3, by comparison of samples at the same concentration, $(MnTPPS_3)_2$ shows the highest signal intensity on $T_1$ weighted images due to highest $T_1$ relaxivity, and MnTCP exhibits significantly higher relaxivity than Gd-DTPA at 3 T. The $r_1$ values, listed in Table 1, also confirmed the high efficacy of MnPs at high field and increased high-field $T_1$ relaxivity per Mn with increased porphyrin size. The $r_1$ values in Table 1 were derived by calculating $T_1$ relaxation times from the inversion-recovery images and then linearly fitting the $T_1$ relaxation rates to obtain the relaxivity $r_1$. $T_2$ relaxivities of the MnPs were also calculated and are listed in

TABLE 1

The relatively weak $T_2$ effect (negative contrast enhancement) does not significantly compromise positive contrast enhancement. Overall, in vitro characterizations suggest that all MnPs are efficient $T_1$ agents and useful for high field applications.

| Table 1: | $T_1$ and $T_2$ relaxivities for the Mn-Porphyrins | |
|---|---|---|
| Porphyrin | $r_1$ (mM$^{-1}$ s$^{-1}$) | $r_2$ (mM$^{-1}$ s$^{-1}$) |
| MnTCP | 7.90 | 9.11 |
| MnTPPS | 8.83 | 10.4 |
| $(MnTPPS_3)_2$ | 14.1 | 18.0 |

MnPs MnTCP and $(MnTPPS_3)_2$ were administered in rats and submitted for MRI studies on a 3T clinical scanner (Philips Achieva), with MnTPPS as a reference, and found to be efficient $T_1$ CAs for in vivo applications, MnTCP and $(MnTPPS_3)_2$. A relatively low dose, 0.05 mmol Mn/kg (typical dose for clinical Gd-based CAs is ~0.1 mmol Gd/kg) was chosen based on the in vitro relaxivity values described above. All MnPs were found to exhibit significant $T_1$ contrast enhancements in vivo after intravenous injection, allowing the pharmacokinetic properties of MnPs, including tissue distribution, metabolic pathway and clearance rate to be analyzed from the in vivo MRI data.

Figure 4:
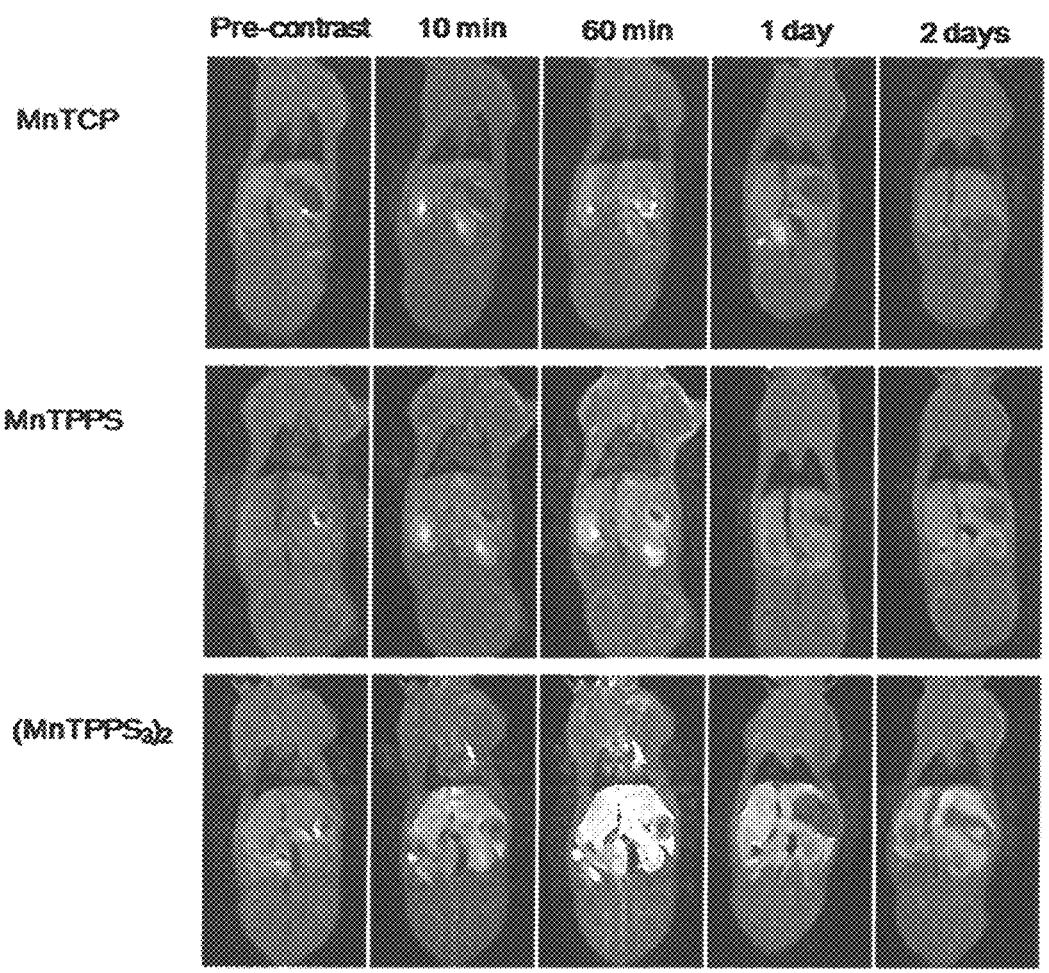
FIG. 4 shows $T_1$-weighted spin-echo MR is at 3 T. A dose of 0.05 mmol Mn/kg of MnTCP, MnTPPS, and $(MnTPPS_3)_2$ was introduced into rats via tail vein injection.

As shown in the whole body images of the rats, FIG. 4, the small and polar MnTCP rapidly accumulated in the kidney within 10 minutes post injection and the majority of kidney enhancement was quickly relocated into the bladder within an hour. The desired rapid clearance of MnTCP via renal filtration was further confirmed by urine sample analysis. The characteristic reddish color of MnPs was clearly visible by eye in the urine samples. The concentrations of MnPs can be accurately quantified by both UV-vis and Mn atomic absorption (Mn AA) spectroscopic analyses. Very high concentrations of MnP were detected in urine 60 minutes (11.7 µM) after injection. Absence of MnTCP in urine sample collected about 24 h post injection suggested complete clearance, similar to Gd-DTPA. In contrast, although MnTPPS showed similar kidney $T_1$ enhancement 10 minutes post injection, the signal lasted significantly longer than MnTCP and was still visible in the image 1 day post-injection. In the same image, the clear liver enhancement suggested a dual-metabolic pathway through both kidneys and liver for MnTPPS, as reported in the literature[25]. The significantly slower renal clearance process of MnTPPS vs MnTCP was confirmed by urine sample analysis. The concentration of MnTPPS 60 min post injection, was 4.41 µM in the urine sample, lower than that of MnTCP. Moreover, a significant amount of MnTPPS (1.12 µM) could still be detected in urine 24 hours post-injection. For the dimeric porphyrin, $(MnTPPS_3)_2$, no bladder enhancement was detected over the three days of the experimental period. Although accumulation was observed in the kidney, the dimer did not cross the glomerulus and did not collect in urine on the tubular side. The exclusion of the renal metabolic pathway for $(MnTPPS_3)_2$ was further confirmed by urine sample analysis. No MnP signal was found by either Mn-AA or UV-vis in urine over the 72 hour post-injection period. The significant liver enhancement suggests that $(MnTPPS_3)_2$ was mainly metabolized by the liver. Noticeably, $(MnTPPS_3)_2$ exhibited relatively long-lasting enhancement in the blood vessels and in the heart. Overall, these observations demonstrated the feasibility of $(MnTPPS_3)_2$ as a blood-pool CA as well as a tissue-selective agent for liver imaging.

As $T_1$ agents, polyporphyrins (two or more covalently linked porphyrin rings) have multiple paramagnetic centers per molecule, and have slower rotational reorientation rates $(T_R)$ to increase the $T_1$ relaxivity, particularly at high magnetic fields according to the SBM theory. For in vivo applications, relatively low doses are needed, reducing toxic exposure of a subject. The size and geometry of a polyporphyrin can be tailored to adjust the pharmacokinetic properties, including diffusion rate, tissue specificity and metabolic pathway to match the different criteria for different applications, such as tissue-specific targeted imaging or dynamic contrast-enhanced (DCE) MRI.

Monomeric water soluble porphyrins can be rapidly cleared through renal filtration after in vivo administration, reducing the exposure time and thus toxicity risk. Monomeric orphyrins can be structurally modified to positively influence the effect of electron configuration on relaxivity. The optimized monomers can then be used directly for in vivo applications or as described herein as building blocks or precursors to dimeric and oligomeric porphyrins.

As indicated above, porphyrin compounds described herein are encompassed by the family of compounds represented by formula (A):

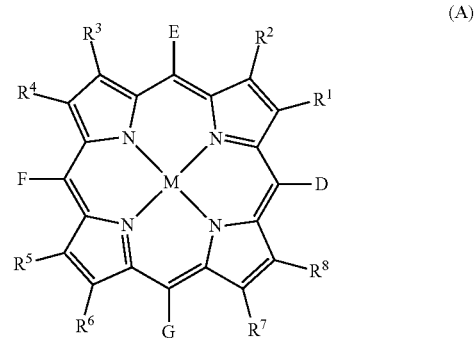

(A)

Ring substituents D, E, F and G are covalently bonded to the meso-positions of the porphyrin ring. The R-groups are covalently bound to the 3- and 4-positions of pyrrole groups of the porphyrin ring.

The compounds are water soluble, so contain at least one water-solubilizing group. Water-solubilizing groups of the invention render a compound suitably soluble in an aqueous medium for use as a CA agent.

Examples of water-solubilizing groups include the anionic groups carboxyl, sulfonate, phosphate (—$OPO_3H_2$), alkylphosphate (—$OPO_3RH$), phosphonate (—$PO_3H_2$), alkylphosphonate (—$PO_3RH$), phosphinate (—$PO_2H$) and alkylphosphinate (—$PO_2R$). The alkyl group of the of an alkylphosphate or alkylphosphonate is typically a straight chain or branched $C_1$-$C_{10}$ alkyl group, e.g., methyl, ethyl, propyl, butyl, pentyl or hexyl.

Examples of water-solubilizing groups include the cationic groups amino, alkylamino, dialkylamino, alkylammonium (—$NR_3^+$), aminoalkyl, guanidine (—NHC(NH)$NH_2$), alkyl guanidine (—NHC(NH)NRH), amido (—C(O)$NH_2$, heterocyclic cations. A heterocylic cation is a cycloalkyl or aryl group containing a nitrogen atom in its ring, e.g. alkyl pyridiums such as methylpyridiniums:

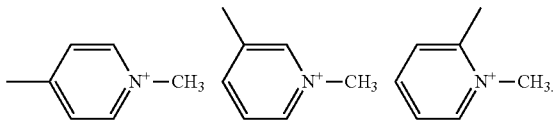

A porphyrin compound such as the MnTCP of the examples can include multiple water-solubilizing groups. Such groups can be anionic, such as the carboxyl group of MnTCP, cationic, or can be a mixture of both, so that the compound can be viewed as zwitterionic. A carbon-based substituent e.g. alkyl containing a water-solubilizing group such as a carboxyl can also contain an amino group and thus also be zwitterionic.

A water-solubilizing group can also be a neutral hydrophilic group, which can be instead of, or in addition to one or more ionic water-solubilizing groups. Such groups include polyols, polyethylene oxides (PEG), diethylene glycol (—$OCH_2CH_2OCH_2CH_2OH$) carbohydrates e.g., glucose, polysaccharides, dextrins, cylclodextrins, amino sugar, glucosamine, glucamine, their derivatives, and the following groups:

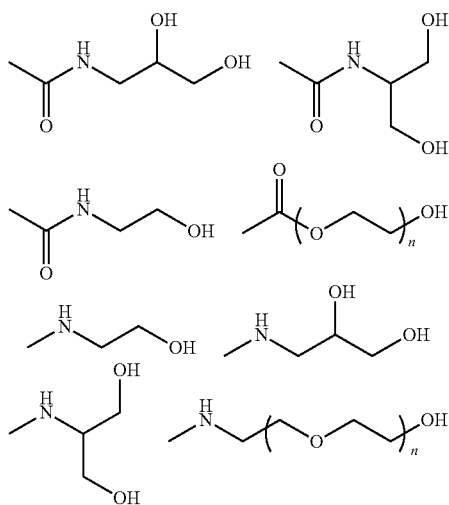

where n=1, 2, 3, 4, 5, 6, 7, 8, 9, 10, 11, 12, 13, 14, 15, 16, 17, 18, 19, or 20.

Water-solubilizing groups that are referred to as ionic are groups are charged at physiological pH. By "physiological pH" or "physiological conditions" is meant water at a pH of about 7.5 and about 37° C., and an ionic strength of about 150 mM. Basic groups, such as amino groups that are converted to positively charged groups under physiological conditions, and acidic groups, such as carboxyl groups that exist as negatively charged groups under physiological conditions are water-solubilizing groups. Under such conditions, at least 10%, but more preferably at least 20%, or at least 30%, or at least 40%, or at least 50%, or at least 60%, or at least 70%, or at least 80%, or at least 90%, or at least 95%, or at least 96%, or at least 97%, or at least 98%, or at least 99% of the water-solubilizing group exists in its charged i.e. ionic form under physiological conditions. Such positively charged groups bearing a proton such as a protonated amino group (ammonium), have a $pK_a$ under such conditions that is less than about 8.5. More preferably, the $pK_a$ is less than 8, or less than 7.5, and more preferably less than 7.0, more preferably still less than 6.5. Likewise, negatively charged groups that are unprotonated under physiological conditions, such as a carboxyl group (carboxylate in unprotonated form), have a $pK_a$ under such conditions that is less than about 8.5. More preferably, the $pK_a$ is less than 8, or less than 7.5, and more preferably less than 7.0, more preferably still less than 6.5.

It is also to be understood that terms such as carboxyl encompass such groups whether or not in ionized form as part of the compound, so cover salts such as sodium carboxylate (—$CO_2^-Na^+$), etc.

As describe elsewhere, in embodiments, carbon atoms of a polyporphyrin ring or rings of a compound can bear one or more substituents i.e., have one or more hydrogens replaced by e.g., an alkyl, aryl group, etc. When such a substituent of a polyporphyrin bears a water solubilising group such as an ionic or hydrophilic group e.g., carboxyl or sulfonate, then the substituent is itself a water solubilising group.

Of course, a monoporphyrin compound can also include one or more substituents such as alkyl groups covalently linked to carbon atoms of the porphyrin ring, and these substituents can bear ionic or hydrophilic water-solubilizing groups.

For use as an MRI agent, a compound is typically soluble in amount of between 10 μM to at least 1 M. Other minimum solubility ranges include from 0.0001 M to 1 M, 0.001 M, 0.01 M to 1 M, 0.1 M to 1 M, or the minimum solubility could be at least 0.0001 M, 0.001 M, 0.01 M or 0.1.

The metal "M" is a paramagnetic metal ion, and includes Mn(II), Mn(III), Fe(II), Fe(III). Gd(III), Cu(I), Cu(II), Ni(II), Ni(I) and Ni(III). Advantageously, the ion can be Mn(II) and Mn(III), also referred to as $Mn^{2+}$ and $Mn^{3+}$, respectively, due to its relatively low toxicity. Mn(III) is preferred among the two oxidation states, due to the higher stability. It is possible for there to be more than one type of metal ion, paramagnetic or diamagnetic to be incorporated as part of a compound. At least one porphyrin ring of a polyporphyrin compound of the invention is metalated with paramagnetic ion, but it is thought preferable that all porphyrin rings of a polyporphyrin compound be metalated for use as an MRI contrast agent.

Porphyrin substituents appended by covalent linkages to the porphyrin rings, when specifically defined, are designated as R-groups, $R^1$, $R^2$, etc., and the letters D, E, F, G, $D^1$, $D^2$, etc. When so-defined, such substituents are monovalent radicals, and it is understood by the skilled person that such groups may be denoted for example as "R" or "—R". So a fluorine radical, for example, may be designated as "F" or "—F" without confusion.

An "alkyl" group indicates the radical obtained when one hydrogen atom is removed from a hydrocarbon. An alkyl group has 1 to 20, 1 to 12, such as 1 to 6, 1 to 5, 1 to 4, 1 to 3, 1 or 2 carbon atoms, or 1 carbon atom. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

A "cycloalkyl" group indicates a saturated cycloalkane radical having 3 to 20 carbon atoms, so can have 3 to 10 carbon atoms, in particular 3 to 8 carbon atoms, such as 3 to 6 carbon atoms, or 6 carbon atoms and includes fused monocyclic, bicyclic, polycyclic, fused, bridged, or spiro polycyclic ring structures, for example, cyclopropyl, cyclobutyl, cyclopentyl, cyclohexyl, or cycloheptyl.

A "heterocycloalkyl" denotes a cycloalkane radical as described above in which one or more $CH_2$ groups atoms e.g., 1, 2, 3 or 4 $CH_2$ groups are replaced by corresponding heteroatoms, O or S, or in which one or more CH groups are replaced by a corresponding heteroatom N, an example of which is piperazinyl.

An "alkenyl" group indicates an alkyl group in which 1, 2, 3, 4 or 5 unsaturations (double bonds) replace a corresponding number of —CHCH— groups, examples being ethenyl, propenyl, butenyl, pentenyl or hexenyl.

A "cycloalkenyl" group indicates mono-, di- tri- or tetra-unsaturated non-aromatic cyclic hydrocarbon radicals such as containing 3 to 20 carbon atoms, including fused monocyclic, bicyclic, polycyclic, fused, bridged, or spiro polycyclic ring structures, and include groups containing 3 to 10 carbon atoms, such as 3, 4, 5 or 6 carbon atoms, e.g. cyclopropenyl, cyclobutenyl, cyclopentenyl, cyclohexenyl, cylcoheptenyl.

A "heterocycloalkenyl" indicates a cycloalkene radical (cycloalkenyl group) in which one or more $CH_2$ groups atoms e.g., 1, 2, 3 or 4 $CH_2$ groups are replaced by corresponding heteroatoms, O or S, or in which one or more CH groups are replaced by a corresponding heteroatom N, examples being dihydrofuranyl and 2,5-dihydro-1H-pyrrolyl.

An "aryl" group is a radical of aromatic carbocyclic rings having 6 to 20 carbon atoms, such as 6 to 14 carbon atoms, or 6 to 10 carbon atoms, particularly 5- or 6-membered rings, that can be fused carbocyclic rings with at least one aromatic ring, such as phenyl, naphthyl, indenyl and indanyl.

A "heteroaryl" group is a radical containing at least one aromatic ring having 1 to 6 O, S and or N heteroatoms, and 1 to 20 carbon atoms, such as 1 to 5 heteroatoms and 1 to 10 carbon atoms, or 1 to 5 heteroatoms and 1 to 6 carbon atoms, in particular 5- or 6-membered rings with 1 to 4 heteroatoms, and can include fused bicyclic rings with 1 to 4 heteroatoms, and wherein at least one ring is aromatic, such as pyridyl, triazolyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

"Arylalkyl" denotes an aryl radical covalently joined to an alkyl group such as a benzyl group.

A "heteroarylalkyl" group indicates a heteroaryl radical covalently joined to an alkyl group.

An "alkynyl" group is a hydrocarbon radical having 1 to 5 triple C—C bonds —C≡C—) and 2 to 20 carbon atoms, typically having 2 to 10 carbon atoms, or 2 to 6 carbon atoms, such as 2 to 4 carbon atoms, examples being ethynyl, propynyl, butynyl, pentynyl or hexynyl.

"Heteroalkyl, heteroalkenyl, heteroalkynyl" refer to alkyl, alkenyl and alkynyl groups, respectively, in which one or more of the carbon atoms (and any associated hydrogen atoms) are each independently replaced with the same or different heteroatoms O, S or N.

"Halogen" indicates a substituent from the seventh main group of the periodic table: fluoro, chloro, bromo and iodo.

The term "haloalkyl" indicates an alkyl group substituted with one or more halogen atoms as defined above, e.g. difluoromethyl. An alkyl optionally substituted with halogen is a haloalkyl when so substituted.

In general, an optional substitution with specified groups, radicals or moieties means that the subsequently described substitution may or may not occur, so that the description includes instances where the circumstance occurs and instances where it does not. An atom with unsatisfied valence(s) is assumed to have the hydrogen atom(s) to satisfy the valences.

"Phosphate" refers to a radical —OP(O)(OR')(OR") where R' and R" are each independently hydrogen, alkyl, cycloalkyl, cycloheteroalkyl, aryl, arylalkyl, heteroalkyl, heteroaryl or heteroarylalkyl.

"Sulfonate" refers to a radical —S(O)(O)OR', where R' is hydrogen, alkyl, cycloalkyl, cycloheteroalkyl, aryl, arylalkyl, heteroalkyl, heteroaryl or heteroarylalkyl.

"Carboxy" or "carboxyl" means the radical —C(O)OH.

The term "hydroxyalkyl" denotes an alkyl group substituted with one or more hydroxyl groups such as hydroxymethyl, hydroxyethyl, hydroxypropyl.

An "alkoxy" group indicates a radical of the formula —OR' in which R' is alkyl such as methoxy, ethoxy, n-propoxy, isopropoxy, butoxy, etc.

The term "alkoxycarbonyl" indicates a radical of the formula —C(O)—O—R' in which R' is alkyl, such as methoxycarbonyl, ethoxycarbonyl, n-propoxycarbonyl, isopropoxy-carbonyl, etc.

The term "alkylcarbonyl" indicates a radical of the formula —C(O)—R' in which R' is alkyl, such as acetyl.

A "heterocyclic ring" includes heteroaryl, heterocycloalkyl and heterocylcoalkenyl and further includes annelated ring systems with each other or with cyclic hydrocarbons.

The term "pharmaceutically acceptable salt" indicates salts formed by reacting a compound of formula (A) with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula (A) may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, glucamine, N-Methylglucamine cycloalkylamines, for example dicyclohexylamine, or benzylamines, for example N,N'-dibenzylethylenediamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

According to various embodiments, a covalent linkage within a compound of formula (A) is provided by, for example, $L^D$, where $L^D$ may be a covalent bond or a bivalent radical that provides the linkage. So here L is a "linker" that links two groups directly covalently as through a bond, or indirectly via a chemical moiety i.e., bivalent radical. Such a bivalent radical corresponds to a monovalent radical obtained when a hydrogen atom is removed therefrom. Where, for example, an aryl or cycloalkyl group provides such linkage and is therefore bivalent, the bivalent aryl or cycloalkyl is referred to as "arylene" or "cycloalkylene", respectively. Examples of these respective groups are thus —$C_6H_4$— and —$C_6H_{10}$—, based on the phenyl and cyclohexyl groups. The terms "alkylene", "alkenylene", "heterocycloalkylene", "cycloalkenylene", "heterocyclo-alkenylene", "heteroarylene", "arylalkylene", "heteroarylalkylene", "alkynylene", "haloalkylene" etc. are similarly derived terms. Other bivalent linkers are —X—C(Y)— in which X and Y are independently selected from the group O, S and NH, and —XC(Y)—Z— in which X, Y and Z are independently selected from the group O, S and NH.

According to various embodiments, a covalent linkage within a compound of formula (A) by $L^D$ where the linker covalently links three groups, as in the moiety (LD'), so the linker is a trivalent radical. Such a trivalent radical corresponds to a bivalent radical obtained when a hydrogen atom is removed therefrom, examples of which are:

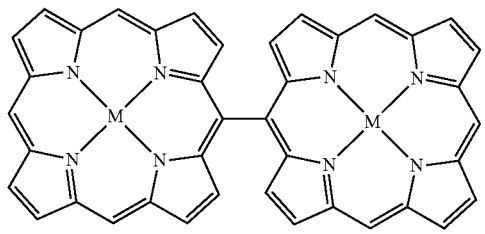

These linkers are referred to herein as "trivalent cyclohexyl" and "trivalent phenyl" groups, respectively, and other trivalent linkers are correspondingly termed.

Linkers, such as those illustrated above, can also bear water-solubilizing groups.

It will thus be appreciated that a variety of water soluble porphyrin compounds useful as MRI contrast agents are made available through this disclosure. In addition to monomeric porphyrins described herein, there are a number of polyporphyrins in which porphyrin rings are covalently linked to each other. As described in greater detail elsewhere herein, one general example is a diporphyrin in which porphyrin rings are directly covalently linked to each other through the meso-positions of the peripheral twenty carbon ring:

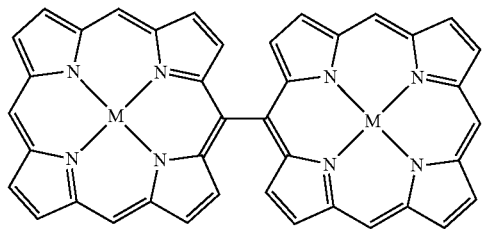

Here, for the sake of simplicity, substituents of porphyring rings are omitted, be they hydrogen atoms, water-solubilizing groups, etc. Porphyrin ring-substitutents can be the same or different from ring to ring of a compound, as can be the paramagnetic metal, M.

Covalent linkage of porphyrin rings can also be provided by a covalent linker:

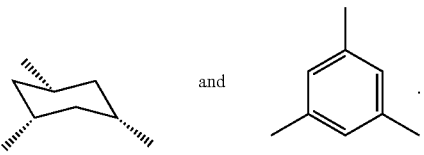

Bivalent covalent linkers, illustrated above as the boxed "L", are described in greater detail elsewhere herein. Again, as for other polyporphyrins described herein, it is possible that porphyrin substitutents be the same or different from ring to ring of a compound, as can be the paramagnetic metal, M.

Particular bivalent linkers include:

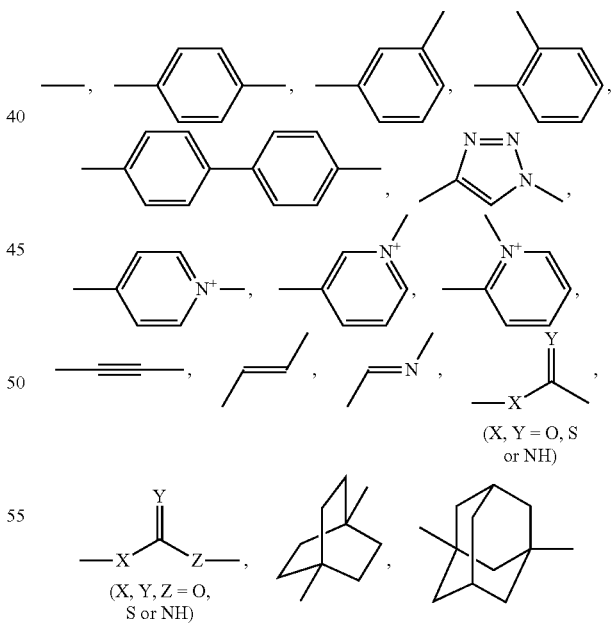

The linkers provide a rigid link between the porphyrin rings i.e., have relatively high conformational rigidity and examples are aromatic ring(s), conjugated or partially conjugated (hyperconjugated) π-bond(s), or rigid systems with saturated bonds, to reduce internal motion.

A rigid linker covalently connects sites in the porphyrin rings, such as carbon atoms in meso-positions of neighboring porphyrin rings, so as to confine movement of those sites with respect to each other within the molecule. So, in aqueous solution at room temperature (21° C.) two porphyrin rings directly connected to each other by a covalent bond between meso-carbons can rotate to some extent with respect to the axis defined by that bond, but the distance between those meso-carbons themselves remains essentially unchanged. The degree to which such distance can vary is possible to determine by molecular modeling methods, such as molecular mechanics calculation. Two such covalently linked porphyrin rings, be it through a bond or linker such as para-carbons of phenyl ring (—$C_6H_4$—), etc., are rigidly linked if the distance between the linking sites does not vary significantly due to conformational changes.

Polyporphyrins can have more than two porphyrin rings covalently linked:

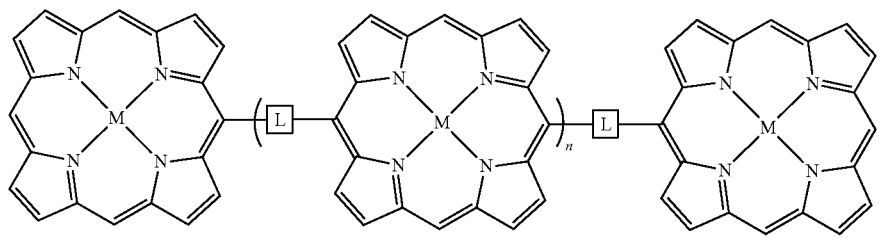

Here, the linker can instead be a covalent bond, and such linkages can be different between rings so that a compound includes different linkers between porphyrin rings, and/or covalent bonds acting as linkages. The number "n" in the foregoing is a whole number used to designate the number of porphyrin rings between the end rings. Various values of n, i.e., 0, 1, 2, 3 . . . etc. are described in greater detail elsewhere herein.

Other arrangements of porphyrin rings are possible, such as:

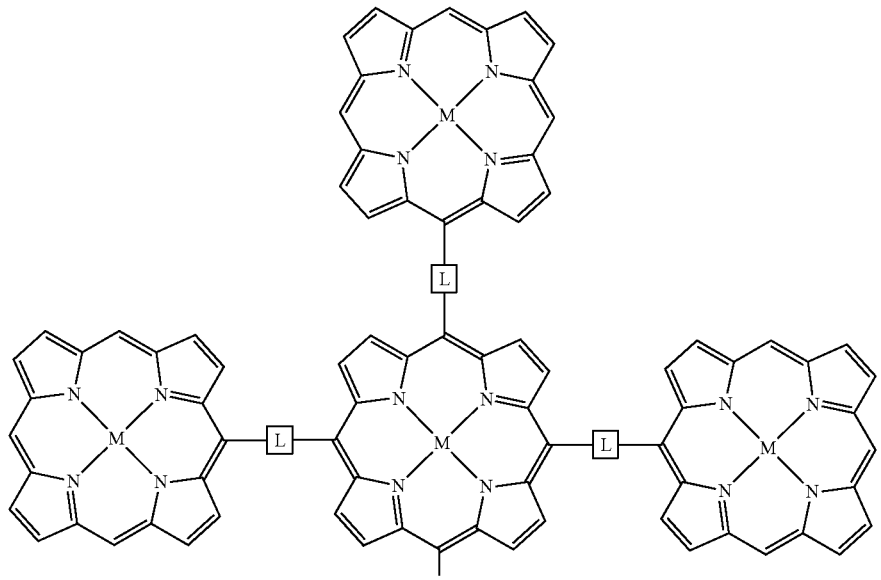

-continued

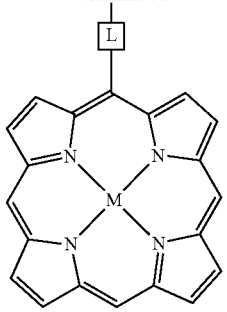

In such configuration, one, two, three or all of the four external porphyrins can have additional porphyrin rings covalently appended thereto as described immediately above. It is also possible that any one of the above-illustrated porphyrin rings be omitted to obtain a configuration in which three porphyrin rings are covalently linked to three meso-positions of a single porphyrin ring, again such linkages being provided by any combination or bivalent linkers or direct covalent bonds. Two of the illustrated porphyrin rings in neighboring positions can be omitted such that a porphyrin ring is linked to a pair of porphyrins through neighboring or vicinal meso-positions of its peripheral carbon ring. Additional porphyrin rings can be appended to one or more meso-positions of the illustrated porphyrins. In the foregoing example of a polyporphyrin, the porphyring ring bound to four porphyrins does not necessarily bear a water-solubilizing group.

Additionally, neighboring porphyrin rings in a compound can be linked by a trivalent linker:

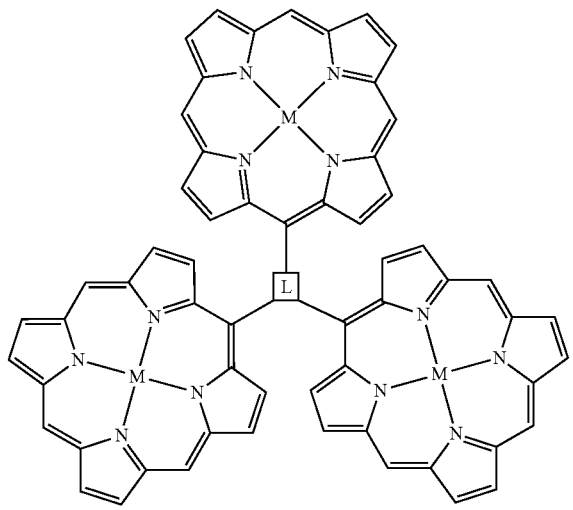

Again, one, two or all three of the illustrated porphyrin rings can further have additional porphyrin ring(s) covalently appended thereto as described for the above-illustrated configurations.

The foregoing examples illustrate polyporphyrin compounds in which all the porphyrin rings are shown as being metalated i.e., containing a paramagnetic metal ion "M". It is possible for one to all of the porphyrin rings to be metalated.

Bivalent and trivalent linkers themselves can bear one or more water-solubilizing groups as well as other substituents.

Compounds of the invention are particularly useful as CAs at relatively high magnetic fields, for example at 1 T or higher, 1.5 T or higher, 3 T or higher, 4.3 T or higher, 7 T or higher, 9.4 T or higher, 11.7 T or higher, and up to 21 T.

As described above, particular compounds exhibit $r_1$ above 4 mM$^{-1}$ s$^{-1}$ at 1T or higher fields.

The present invention provides CAs that can be used to generate an image of a human or non-human subject involving administering the contrast agent to the subject e.g., vascularly, via the gastrointestinal tract, etc. and generating an image of at least a part of the subject to which the contrast agent has been distributed.

Known methods for administering diagnostics can be used to administer CAs. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. These solutions are typically sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected. The invention further provides formulations comprising CA and a pharmaceutically acceptable excipient, wherein the CA is formed according to any of the embodiments described herein, and wherein the formulation is suitable for administration as an imaging enhancing agent and the CA is present in an amount sufficient to enhance an MRI image. These agents can be administered by any means in any appropriate formulation. Detergents can also be used to stabilize the composition or the increase or decrease the absorption of the composition. Other physiologically acceptable compounds include wetting agents, emulsifying agents, dispersing agents or preservatives that are particularly useful for preventing the growth or action of microorganisms. One skilled in the art would appreciate that the choice of acceptable carrier, including a physiologically acceptable compound depends, e.g. on the route of administration and on the particular physio-chemical characteristics of any co-administered agent.

Methods of introduction include, but are not limited to, intradermal, intramuscular, intraperitoneal, intravenous, subcutaneous, intranasal, rectal, vaginal, and oral routes. A CA composition may be administered by any convenient route, for example by infusion or bolus injection, by absorption through epithelial or mucocutaneous linings e.g., oral mucosa, vaginal, rectal and intestinal mucosa, etc., and may be administered together with other biologically active agents. Administration can be systemic or local. In addition, a CA composition may be introduced into the central nervous system by any suitable route, including intraventricular and intrathecal injection; intraventricular injection may be facilitated by an intraventricular catheter, for example, attached to a reservoir, such as an Ommaya reservoir. A CA composition can be delivered by any means known in the art systematically e.g., intravenously, regionally or locally e.g. intra- or peri-tumoral or intra-cystic injection, e.g. to image bladder cancer by e.g., intra-arterial, intra-tumoral, intravenous, parenteral, intra-pneural cavity, etc. For example, intra-arterial injections can be used to have a regional effect e.g. to focus on a specific organ (e.g. brain, liver, spleen, lungs). For example intra-hepatic artery injection or intra-carotid artery injection may be used. If it is decided to deliver the preparation to the brain, it can be injected into a carotid artery or an artery of the carotid system of arteries e.g., ocipital artery, auricular artery, temporal artery, cerebral artery, maxillary artery, etc. The present invention includes pharmaceutical compositions which include a CA alone or with a pharmaceutically acceptable carrier.

An embodiment of the invention is a method of detecting a condition in which cells express a characteristic surface protein. The method includes administering to the cells a CA comprising a compound of the invention that is coupled to an agent which binds to the protein, and obtaining an MRI image of the cells. The condition can be a lung disease, emphysema, asthma, a cancer, particularly breast, prostate, or brain cancer, ischemia, particularly stroke, cardiac infarct, muscle ischemia, chronic kidney disease, or liver disease, particularly cirrhosis or cancer of the liver. Administering the CA to cells can be in vivo or in vitro.

The invention is also a method for monitoring transport of an effector agent to a target found within a cell. This aspect includes contacting the cell with a delivery vehicle encapsulating the agent and a CA described herein, and obtaining an MRI image of the cell. The delivery vehicle can be a nanoparticle, a nanocapsule or a liposome.

The invention is also a method of labeling a cell. The method includes administering to the cell a CA comprising a compound of the invention coupled to an agent which binds to cell. The method can further include detecting the labeled cell by obtaining an MRI image thereof. The agent can be an antibody.

The invention includes a method of screening for therapeutic agents useful in the treatment of a disease. This can include contacting a molecule comprising a test compound coupled to a CA disclosed herein and contacting the molecule with a target cell, and detecting the labeled cell by obtaining an MRI image thereof.

A CA and agent that includes coating material may be made up of, for example, nanoparticles or nanocapsules, liposomes and the like. A suitable means is the encapsulation in biodegradable polymers with controllable release, such as polylactide and/or polyglycolide. In this context, the coating material may be chosen such that the agent is released in a predetermined manner. Such coating materials have been described in the literature and the skilled worker can select, from a multiplicity of materials, the material best suited to the purpose in hand.

The agent and CA are encapsulated with the encapsulation material, or coated therewith, in a known manner. Encapsulation means that the agent is shielded by the polymer from the physiological environment, such that it is not altered or degraded until it arrives at the target. The encapsulation may be only one layer which surrounds the CA and agent, but it may also be a liposome or nanoparticle or microparticle in which the agent is embedded or enclosed. It may also be enclosed by complexing. A CA and agent may be covalently coupled to each other prior to encapsulation. A person skilled in the art is familiar with various forms of encapsulation or coating of agents, which can be employed as long as they do not interfere with the binding of e.g., the target-finding agent to its receptor and the introduction of the agent into the cell, and release the agent in the cell. The encapsulation of the agent with the encapsulation material, and/or the preparation of suitable particles, can be done using customary methods. In the simplest embodiment, the active agent is mixed with the encapsulation material, for example a cationic polymer, such as polyethyleneimine, if appropriate in dissolved form.

Liposomes may comprise a lipid such as phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides, cerebrosides and combinations thereof; a cationic lipid (or other cationic amphiphile) such as 1,2-dioleyloxy-3-(trimethylamino)propane (DOTAP); N-cholesteryloxycarbaryl-3,7,12-triazapentadecane-1,15-diamine (CTAP); N-[1-(2,3,-ditetradecyloxy)propyl]-N,N-dimethyl-N-hydroxyethylamm-onium bromide (DMRIE); N-[1-(2,3,-dioleyloxy)propyl]-N,N-dimethyl-N-hydroxy ethylammonium bromide (DOME); N-[1-(2,3-dioleyloxy)propyl]-N,N,N-trimethylammonium chloride (DOTMA); 3 beta [N—(N',N'-dimethylaminoethane)carbamoly]cholesterol (DC-Choi); and dimethyldioctadecylammoniurn (DDAB); dioleoylphosphatidyl ethanolamine (DOPE), cholesterol-containing DOPC; and combinations thereof; and/or a hydrophilic polymer such as polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxylmethylcellulose, hydroxyethylcellulose, polyethyleneglycol, polyaspartamide and combinations thereof.

EXAMPLES

In general, monomeric porphyrins can be synthesized based on the Lindsey method[20] from pyrrole and the corresponding aldehydes. Monomers can then be used directly, or after necessary functional group transformations, to build dimeric, oligomeric or polymeric porphyrins using coupling reactions. After installation of water solubilizing groups, paramagnetic ions e.g., manganese ions are inserted into the porphyrin cores to generate the final products. The sequence of these reaction steps can be varied in certain cases. Examples for reaction steps are described below.

Synthesis of Porphyrin Building Blocks

Using different compositions of aldehydes and pyrrole, different porphyrin monomers can be obtained by a Lindsey reaction[20], as exemplified in Scheme 1. Both symmetric ($R_1=R_2=R_3=R_1$) or non-symmetric (at least two R groups are different) porphyrins can be obtained.

Scheme 1 General method for synthesis of symmetric or non-symmetric porphyrin monomers.

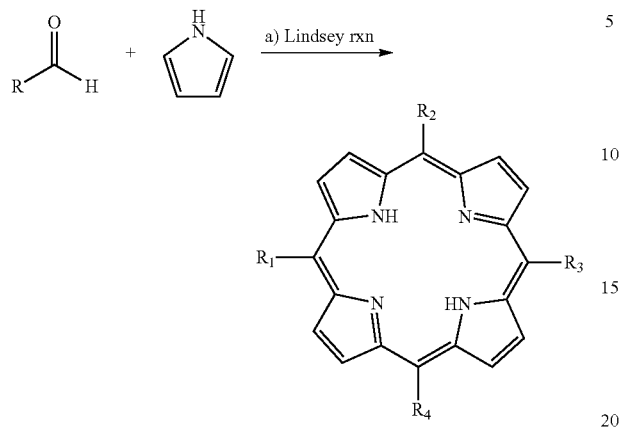

For certain porphyrin building blocks, protection or functional group trans-formation is necessary before they can be coupled together. Two examples are shown in Scheme 2, including protection of the porphyrin core by zinc insertion and bromination on the porphyrin meso-position.

Scheme 2 Zinc insertion and bromination of porphyrins.

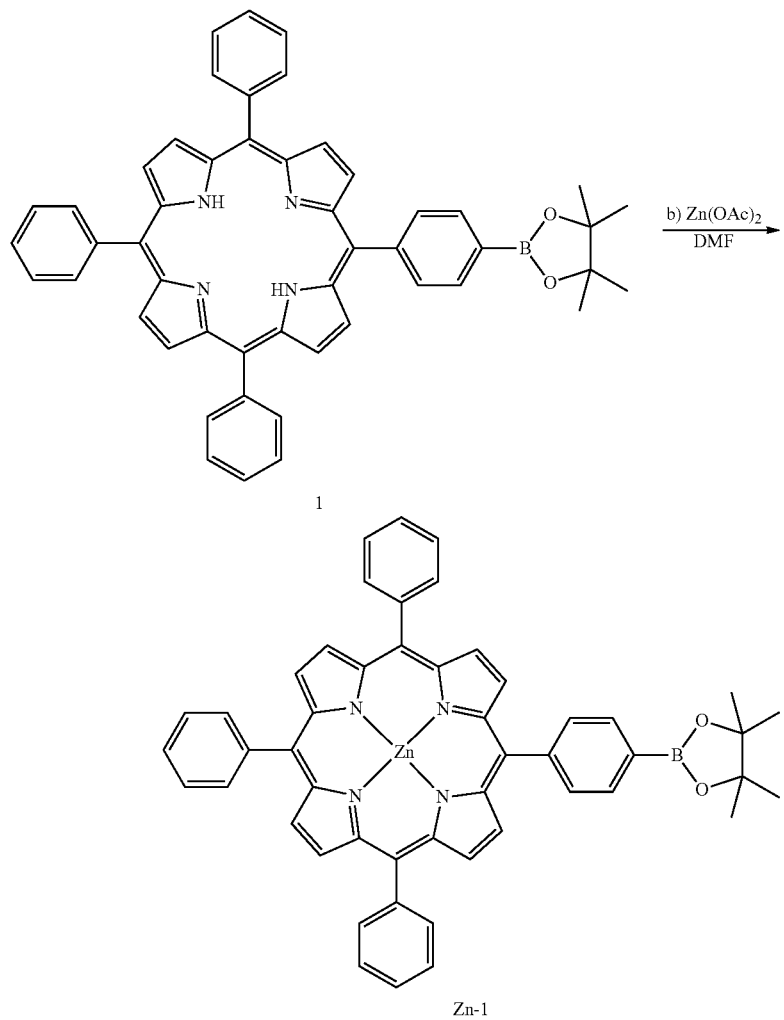

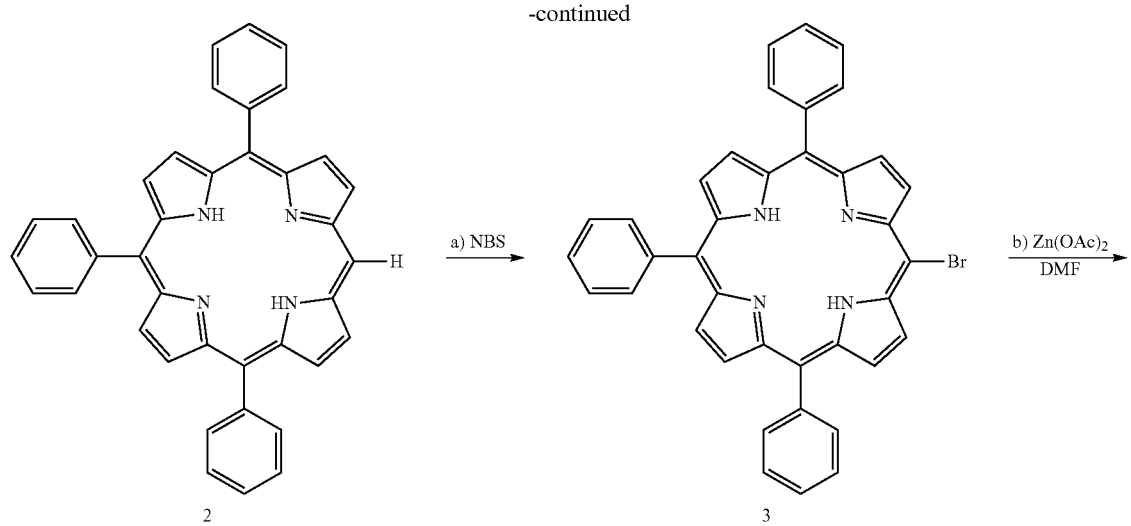

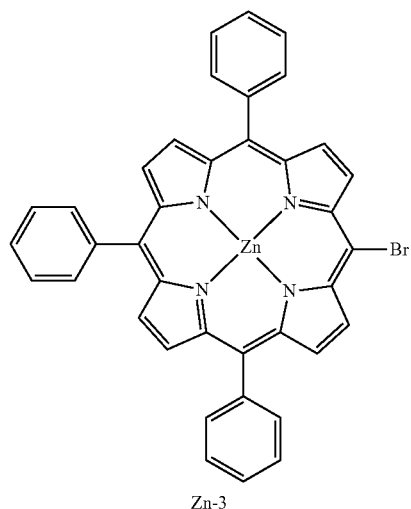

Coupling of Porphyrins

In principle, coupling chemistry can be applied to porphyrin building blocks with complimentary functional groups. Scheme 3 shows examples of three different coupling reactions, including oxidative coupling reaction with hypervalent iodine, Suzuki coupling, and Pd(II)-catalyzed homolytic coupling that could be applied for linking porphyrin rings.

(A)
Scheme 3 Coupling reactions for the synthesis of porphyrin oligomers. a) PhI(OCO-CF$_3$)$_2$ (PIFA), b) Suzuki coupling: 2:1 Tol:DMF, Cs$_2$CO$_3$, Pd(PPh$_3$)$_4$, c) Tetra-n-butylammonium fluoride (TBAF), Pd(PPh$_3$)$_2$Cl$_2$, THF:H$_2$O 4:1, air, RT
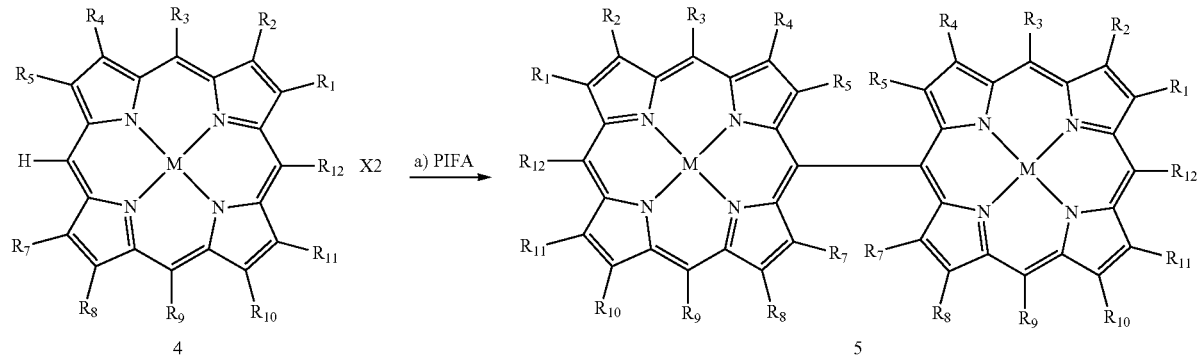
(B)
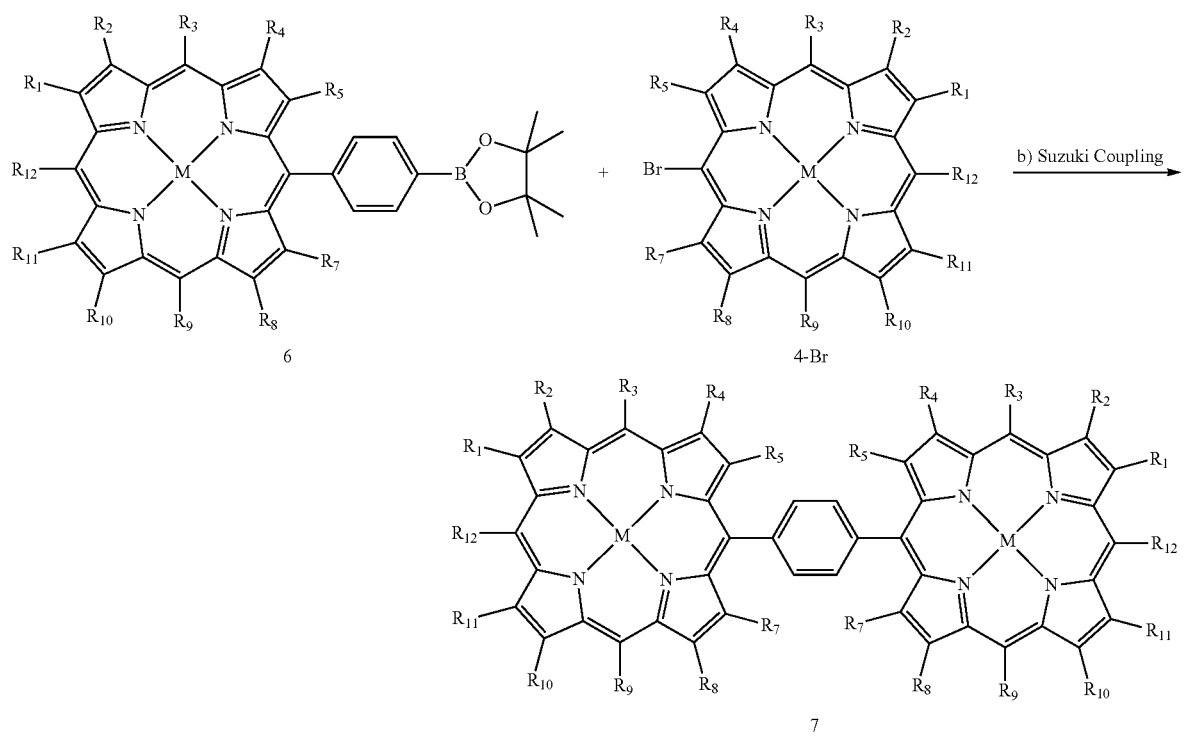
(C)
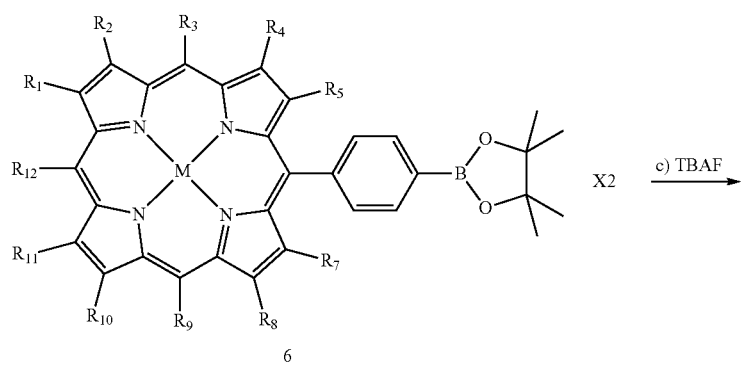

-continued

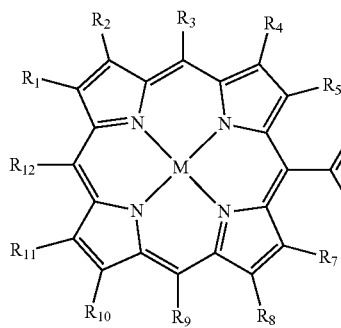
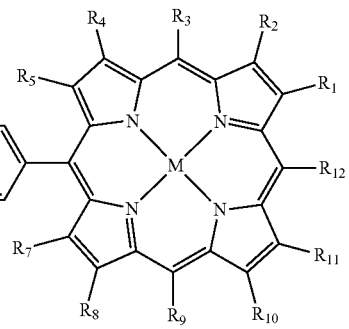

8

Installation of Water Solubilizing Groups and Mn-Insertion

The final MnPs should be water-soluble for in vivo applications. The polar and water-solubilizing groups, such as sulfonates or carboxylates can be introduced by different methods. By sulfonation reaction with concentrated sulfuric acid, the sulfonates can be installed on the phenyl groups attached to the porphyrin meso-position; the carboxylate groups can be generated from the hydrolysis of ester groups pre-installed on the porphyrins. Mn can be inserted into the porphyrins, either before or after the introduction of water-solubilizing groups, as exemplified in Scheme 4.

Scheme 4 Examples of introducing sulfonates or carboxylates, and the insertion of Mn in porphyrins. a) Sulfonation: conc. $H_2SO_4$ 80° C., 9 h; b) Mn insertion: $Mn(OAc)_2$ or $MnCl_2$, DMF, reflux c) 2M NaOH, THF, EtOH, reflux, 12 h

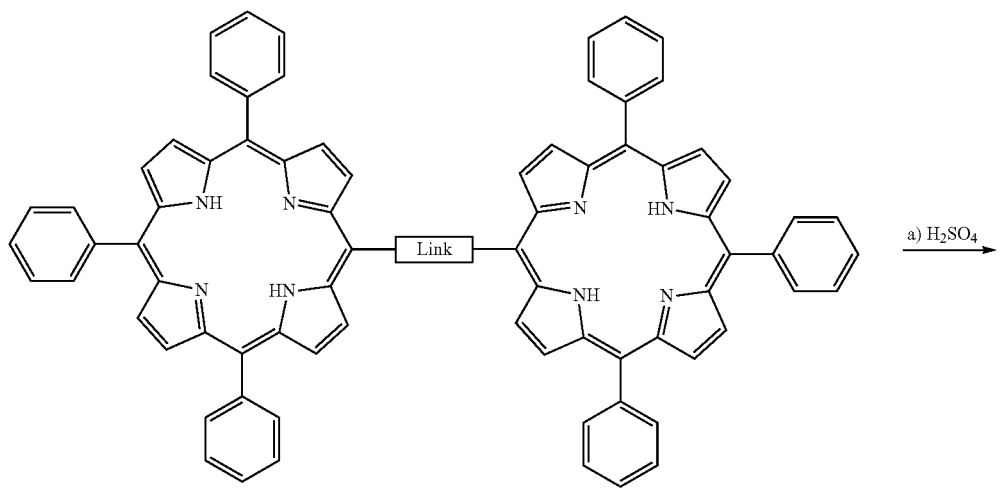

9

-continued
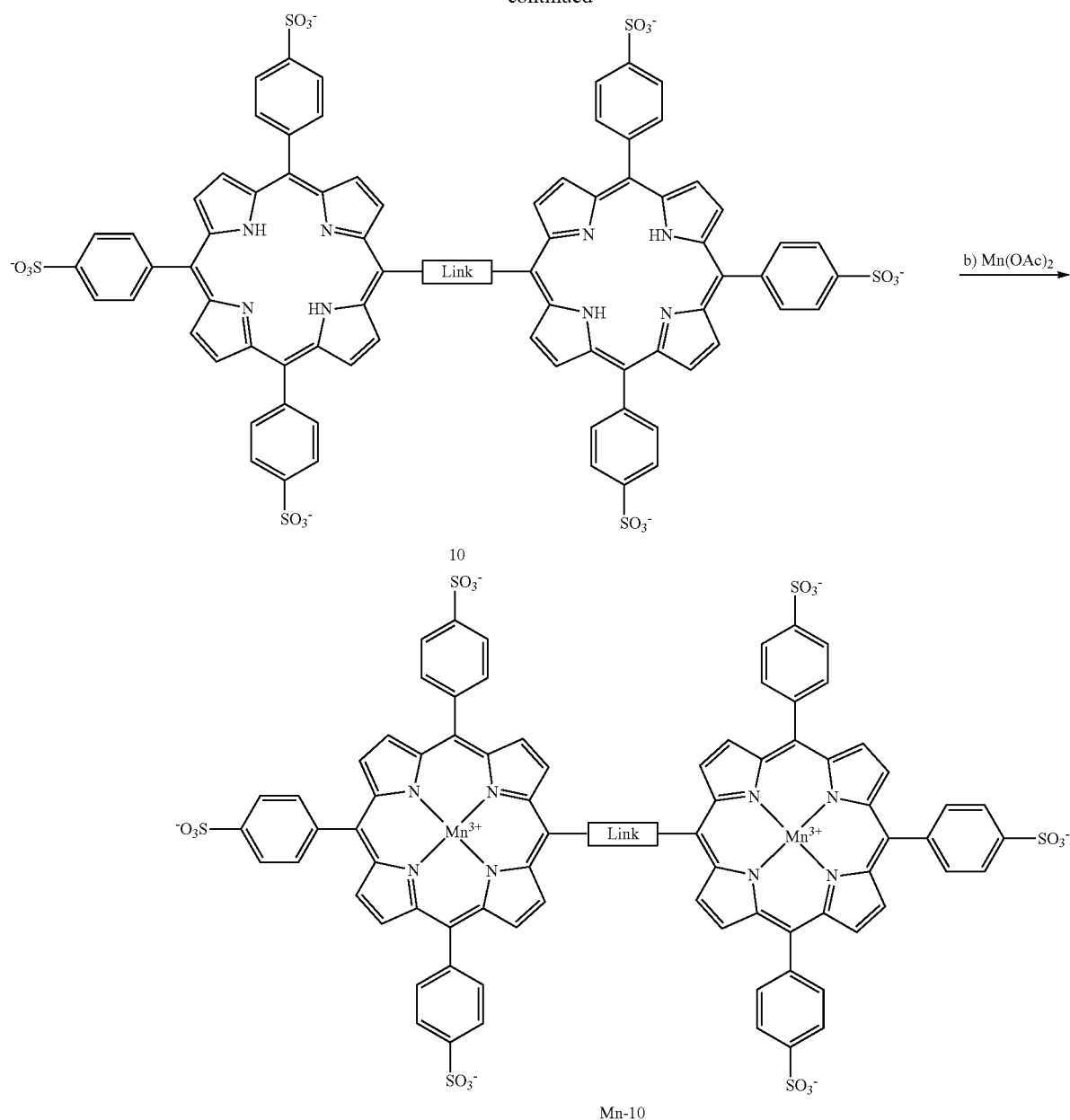
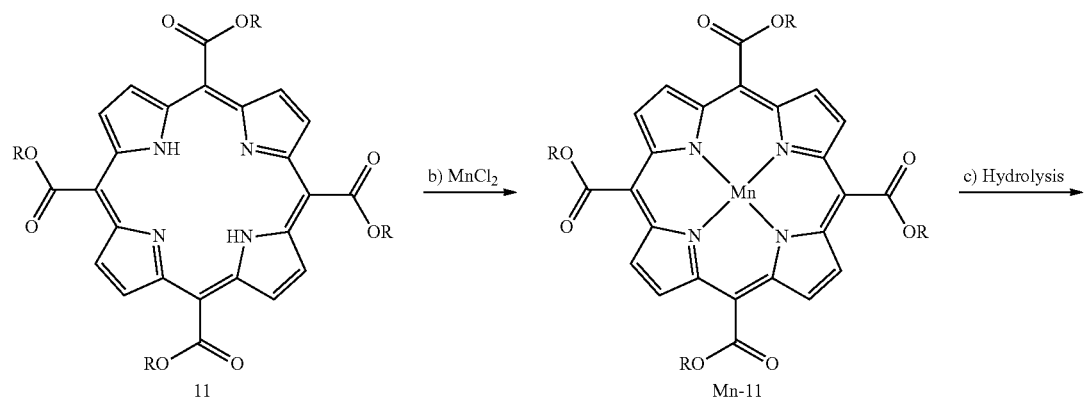

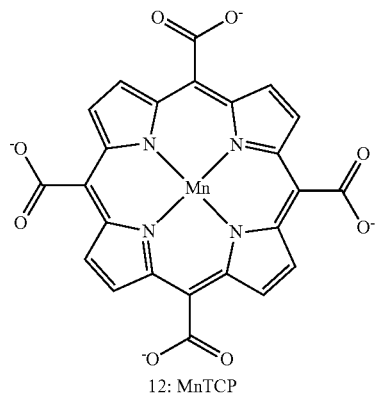

12: MnTCP

Synthetic Procedures

All reagents and solvents were of commercial reagent grade and were used without further purification except where noted. $^1$H NMR spectra were performed at 500 MHz. Mass spectra were obtained on electron-spray ionization mode. UV-vis spectra were recorded on an Agilent 8453 UV-Visible Spectroscopy Systems. Column Chromatography was carried out using Calcdon Silica Gel 60; 50-200 microns 70-300 mesh, or using Sephadex™ LH-20 with dry bead size of 18-111 μm from GE Health Care Dialysis was performed with Sigma Aldrich Pur-A-Lyzer™ Mega 3500/1000 MWCO. Reverse Phase column was loaded with Agela Technologies C18 Flash 40-60 μm. Cation ion exchange was performed using an Amberlite® IR120, H resin.

(a) Synthesis of Porphyrin 1[21]

2.31 g (9.9 mmol) of 4-boronopinacolbenzaldehyde was added to a RB flask. 3.0 ml (30 mmol) of benzaldehyde was then added followed by 400 ml of anhydrous dichloromethane. The flask was sealed and $N_2$ was bubbled through for 20 min. 2.79 ml (40.2 mmol) of freshly distilled pyrrole was added together with 0.63 ml of $BF_3 \cdot OEt_2$ (12.4 mM). After 1 h of reflux in the dark, 7.94 g (35 mmol) of DDQ was added and the reaction was allowed to reflux for another 1 h. The solution was filtered with basic alumina and column chromatography with 6:4 dichloromethane-hexane solvent system was run through silica to remove TPP. The solvent was switched to 8:2 dichloro-methane-hexane to elute the product. The product (30 mg) was isolated with 4% yield, characterized by NMR and MS. $^1$H NMR (500 MHz, $CDCl_3$): δ 8.84 (8H, s, por-β), 8.18-8.25 (10H, m, Ph), 7.72-7.78 (9H, m, Ph), 1.50 (12H, s, alkyl), −2.78 (2H, s, NH). ESI MS found m/z=741.3 ([M+H]$^+$), calcd for $C_{50}H_{42}BN_4O_2^+$, m/z=741.3.

(b) Synthesis of Porphyrin (TPP)$_2$[22]

73.6 mg (1 eqv) of 1, 9.0 mg of $Pd(PPh_3)_2Cl_2$ (0.1 eqv), 35 mg of tetrabutylammonium fluoride (1 eqv), were added to a pear shaped flask. 10 ml of 2:8 water and THF solvent mixture was added and allowed to stir at room temperature and opened to oxygen. After 5.5 h, the reaction was stopped and dried by rotavap. The product is barely soluble in chloroform and diethyl ether, thus hexane:chloroform 7:3 and diethyl ether were used to rinse off porphyrin impurities. Filtration was performed and the purple crystals residue were rinsed with cold $CHCl_3$. 48.5 mg of product was obtained (80%). $^1$H NMR (500 MHz, $CDCl_3$): δ 9.06 (4H, d, J=4.7 Hz, por-β), 8.94 (4H, d, J=4.7 hz, por-β), 8.88 (8H, s, por-β), 8.47 (4H, d, J=8.1 Hz, Ph), 8.35 (4H, d, J=8.1 Hz, Ph), 8.30-8.21 (6H, m, Ph), 7.84-7.72 (9H, m, Ph), −2.71 (2H, s, NH). ESI MS found m/z=1227.5 ([M+H]$^+$), calcd for $C_{88}H_{58}N_8$, m/z=1227.5.

(c) Sulfonation of Porphyrin (TPP)$_2$ to Produce (TPPS$_3$)$_2$, Modified from the Literature Method[23]

30 mg of (TPP)$_2$ was allowed to react in 2 ml of conc. Sulfuric acid at 80° C. for 9 h. The solution turned from red to green upon acidifying. After the reaction, the porphyrin solution was poured into a beaker of ice, diluted and neutralized with 1 M NaOH until the solution turned deep red. The solution was concentrated and the porphyrin solution was rinsed off from $Na_2SO_4$ salt with cold water. The porphyrin solution was dialyzed using a 3500 MWCO membrane to remove the excess salt. 40 mg of product was obtained (96%). $^1$H NMR (500 MHz, DMSO-$d_6$): δ 9.06 (4H, d, J=4.6 Hz, por-β), 8.98 4H, d, J=4.6 Hz, por-β), 8.87 (8H, s, β), 8.49 (8H, m, Ph), 8.25-8.15 (12H, m, Ph), 8.12-8.00 (12H, m, Ph), −2.86 (4H, s, NH). ESI MS found m/z=283.4 ([M]$^{6-}$), calcd for $C_{88}H_{48}N_8O_{18}S_6^{6-}$, m/z=283.4.

(d) Mn Insertion into Porphyrin (TPPS$_3$)$_2$ to Produce (MnTPPS$_3$)$_2$ 10.7 mg (5 eqv) of $Mn(OAc)_2$ and 10 mg (1 eqv) of (TPPS$_3$)$_2$ was used for Mn insertion. The reaction occurred for overnight at 115° C. with stirring in 3 ml of DMF. DMF was removed by distillation. The crude product was dried and dissolved in pure water. Dialysis was used to separate bulk excess salt. RP column was subsequently used to remove excess salt. Ion-exchange column was used to replace possible $Mn^{2+}$ counter ions into $Na^+$ ions. 11 mg (97%) of dark green solid product was obtained. ESI MS found m/z=451.5048 ([M]$^{4-}$), calcd for $C_{88}H_{48}N_8O_{18}S_6Mn_2^{4-}$, m/z=451.5047. UV-vis (HEPES buffer, pH=7.0) $\lambda_{abs}$=382, 402, 421, 469, 569, 602 nm.

(e) The Synthesis of 5,10,15,20-tetrakis(ethoxycarbonyl)porphyrin, 11

The procedure was performed with a slight modification of the literature method.[24] Ethyl glyoxalate (50% in toluene, 1.88 ml, 9.4 mmol) in dichloromethane and pyrrole (0.65 ml, 9.4 mmol) were stirred at room temperature, in the dark and under an argon atmosphere. After 10 min $BF_3 \cdot OEt_2$ (42 ml, 3.10 mmol) was added drop wise. The reaction was stirred at room temperature for 1.25 h followed by the addition of DDQ (1.5999 g, 7.05 mmol). After a stirring period of 2.25 h NEt$_3$ (0.43 ml, 3.06 mmol) was added via syringe and the reaction mixture was concentrated on a rotary evaporator. The crude solution was suction filtered over sealite using DCM as an elution solvent. The solution was concentrated on a rotary evaporator. Purification by column chromatography (DCM) on silica gel gave 169.2 mg (12%) of compound 7 as a black-purple solid. $^1$H NMR (500 MHz, CDCl$_3$) 9.52 (8H, s, por-β), 5.11 (8H, q, J=7.2 Hz), 1.81 (12H, t, J=7.2 Hz), −3.33 (2H, s, NH). UV-vis (DCM) $\lambda_{max}$=409 nm.

(f) The Synthesis of [5,10,15,20-tetrakis(ethoxycarbonyl)porphyrinato]manganese(III) Chloride, Mn-11

The current step was performed according to the literature method.[24] Compound 11 (17.8 mg, 29.7 μmol) was dissolved in 2 ml of DMF. MnCl$_2$.4H$_2$O (17.7 mg, 89.2 μmol) was added and the reaction was refluxed open to air for 5 h. The reaction was stirred at room temperature open to air for a further 11.5 h. Distillation of DMF resulted in a black-purple solid. Purification by stepped gradient column chromatography (eluting with DCM to 7% MeOH in DCM) on silica gel gave 16.5 mg (85%) of compound Mn-11 as a black-purple solid. ESI MS found m/z=651.1 ([M]$^+$), calcd for C$_{32}$H$_{28}$MnN$_4$O$_8^+$, m/z=651.1. UV-vis (MeOH) $\lambda_{abs}$=328, 366, 387, 413, 456, 552 nm.

(g) Synthesis of [5,10,15,20-tetrakis(carboxy)porphyrinato]manganese(III) Chloride, MnTCP Ethanol (10 ml) and 2 M NaOH$_{(aq)}$ (10 ml) were added to a solution of 7 (14.3 mg, 21.9 μmol) in 6 ml of THF. The reaction was refluxed for 12 h followed by neutralization with 3 M H$_2$SO$_{4(aq)}$. Purification by sephadex LH-20 chromatography with ultrapure water gave the desired product in 85% yield. ESI MS found m/z=539.0030 ([M]$^+$), calcd for C$_{24}$H$_{12}$MnN$_4$O$_8^+$, m/z=539.0034. UV-vis (Hepes buffer, pH=7.0) $\lambda_{abs}$=325, 377, 397, 421, 465, 561, 592 nm.

REFERENCES

1. Lauterbur, P. C., Image Formation by Induced Local Interactions: Examples Employing Nuclear Magnetic Resonance. *Nature* 1973, 242 (5394), 190-191.
2. Hinshaw, W. S.; Bottomley, P. A.; Holland, G. N., Radiographic thin-section image of the human wrist by nuclear magnetic resonance. *Nature* 1977, 270 (5639), 722-723.
3. Number of magnetic resonance imaging (MRI) units and computed tomography (CT) scanners. http://www.cdc.gov/nchs/data/hus/2010/120.pdf (accessed Aug. 28, 2012).
4. Seeing the World Through Chemical Imaging (poster). http://wwvw.nap.edu/html/11994/ChemPoster.pdf (accessed Aug. 29, 2012).
5. Contrast Media: A Market Snapshot. http://www.researchandmarkets.com/reports/1195353/ (accessed Aug. 28, 2012).
6. Merbach A E, T. E., *The Chemistry of Contrast Agents in Medical Magnetic Resonance Imaging.* John Wiley & Sons, Ltd: Chichester, 2001; p 471.
7. Caravan, P., Strategies for increasing the sensitivity of gadolinium based MRI contrast agents. *Chemical Society Reviews* 2006, 35, 512-523.
8. Langereis S., D. A., Tilman M. Hackeng, Marcel H. P. van Genderen and E. W. Meijer, Dendrimers and magnetic resonance imaging. *New J. Chem.* 2007, 31, 1152-1160.
9. Ardenkjaer-Larsen, J. H.; Fridlund, B.; Gram, A.; Hansson, G.; Hansson, L.; Lerche, M. H.; Servin, R.; Thaning, M.; Golman, K., Increase in signal-to-noise ratio of >10,000 times in liquid-state NMR. *Proceedings of the National Academy of Sciences* 2003, 100 (18), 10158-10163.
10. Abragam, A., *Principles of Nuclear Magnetism.* Oxford University Press: Oxford, 1961.
11. Rudin, M.; Beckmann, N.; Porszasz, R.; Reese, T.; Bochelen, D.; Sauter, A., In vivo magnetic resonance methods in pharmaceutical research: current status and perspectives. *NMR in Biomedicine* 1999, 12 (2), 69-97.
12. Hoult, D. I., Sensitivity and Power Deposition in a High-Field Imaging Experiment. *Journal of Magnetic Resonance Imaging* 2000, 12 (1), 46-67.
13. Schick, F., Whole-body MRI at high field: technical limits and clinical potential. *European Radiology* 2005, 15 (5), 946.
14. Rohrer, M.; Bauer, H.; Mintorovitch, J.; Requardt, M.; Weinmann, H.-J., Comparison of Magnetic Properties of MRI Contrast Media Solutions at Different Magnetic Field Strengths. *Investigative Radiology* 2005, 40 (11), 715-724.
15. Public Health Advisory—Gadolinium-containing Contrast Agents for Magnetic Resonance Imaging (MRI). http://www.fda.gov/DrugsDrugSafety/PostmarketDrug-SafetyInformationforPatientsand Providers/DrugSafety-InformationforHeathcareProfessionals/PublicHealthAdvisories/uc m053112.htm.
16. Mohs, A. M.; Lu, Z.-R., Gadolinium(III)-based blood-pool contrast agents for magnetic resonance imaging: status and clinical potential. *Expert Opinion on Drug Delivery* 2007, 4 (2), 149-164.
17. Chen, C. w.; Cohen, J. S.; Myers, C. E.; Sohn, M., Paramagnetic metalloporphyrins as potential contrast agents in NMR imaging. *FEBS Letters* 1984, 168 (1), 70-74.
18. Koenig, S. H.; III, R. D. B.; Spiller, M., The anomalous relaxivity of Mn$^{3+}$TPPS$_4$. *Magnetic Resonance in Medicine* 1987, 4 (3), 252-260.
19. Kolarova, H.; Macecek, J.; Nevrelova, P.; Huf, M.; Tomecka, M.; Bajgar, R.; Mosinger, J.; Strnad, M., Photodynamic therapy with zinc-tetra(p-sulfophenyl)porphyrin bound to cyclodextrin induces single strand breaks of cellular DNA in G361 melanoma cells. *Toxicology in Vitro* 2005, 19 (7), 971-974.
20. Lindsey, J. S.; Schreiman, I. C.; Hsu, H. C.; Kearney, P. C.; Marguerettaz, A. M., Rothemund and Adler-Longo reactions revisited: synthesis of tetraphenylporphyrins under equilibrium conditions. *The Journal of Organic Chemistry* 1987, 52 (5), 827-836.
21. Holmes, A. E.; Das, D.; Canary, J. W., Chelation-Enhanced Circular Dichroism of Tripodal Bisporphyrin Ligands. *Journal of the American Chemical Society* 2007, 129 (6), 1506-1507.
22. Seganish, W. M.; Mowery, M. E.; Riggleman, S.; DeShong, P., Palladium-catalyzed homocoupling of aryl halides in the presence of fluoride. *Tetrahedron* 2005, 61 (8), 2117-2121.
23. Srivastava, T. S.; Tsutsui, M., Unusual metalloporphyrins. XVI. Preparation and purification of tetrasodium meso-tetra(p-sulfophenyl)porphine. Easy procedure. *The Journal of Organic Chemistry* 1973, 38 (11), 2103-2103.

24. Trova, M. P.; Gauuan, P. J. F.; Pechulis, A. D.; Bubb, S. M.; Bocckino, S. B.; Crapo, J. D.; Day, B. J., Superoxide dismutase mimetics. Part 2: synthesis and structure—Activity relationship of glyoxylate- and glyoxamide-Derived metalloporphyrins. *Bioorganic & Medicinal Chemistry* 2003, 11 (13), 2695-2707.

25. SCHMIEDL, U. P.; NELSON, J. A.; STARR, F. L.; SCHMIDT, R., Hepatic Contrast-Enhancing Properties of Manganese-Mesoporphyrin and Manganese-TPPS4: A Comparative Magnetic Resonance Imaging Study in Rats. *Investigative Radiology* 1992, 27 (7), 536-542.

What is claimed is:

1. A water soluble porphyrin compound of formula (A), or a salt thereof:

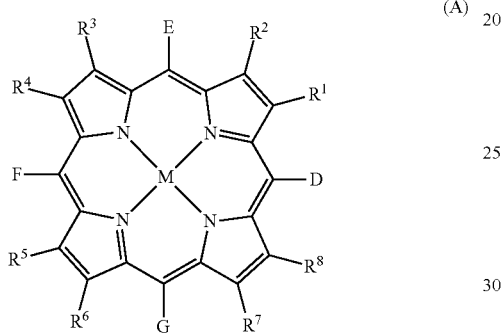

(A)

wherein:
each of $R^1$ to $R^8$ and D, E, F and G is independently selected from the group consisting of:
hydrogen, halogen, thiol, cyano, nitro, amido (—C(O)NH$_2$), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), alkylammonium (—NR$_3^+$), guanidine (—NHC(NH)NH$_2$), alkyl guanidine (—NHC(NH)NRH), amido (—C(O)NH$_2$, a C$_3$-C$_6$ cycloalkyl group containing a nitrogen atom in its ring wherein the cycloalkyl group is bonded to the porphyrin ring by a carbon or nitrogen atom, a C$_3$-C$_6$ aryl group containing a nitrogen atom in its ring, and

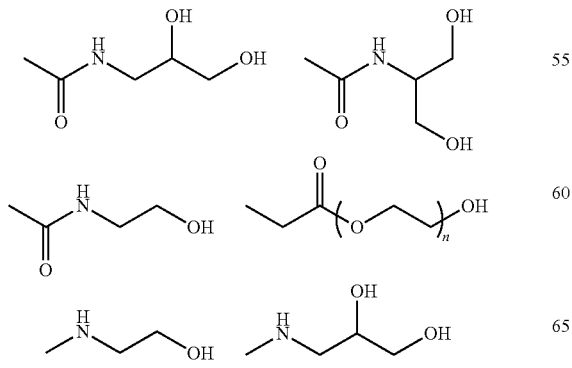

wherein n is from 1 to 20;

C$_1$-C$_6$ alkyl, optionally substituted with up to 4 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl, guanidine (—NHC(NH)NH$_2$), alkyl guanidine (—NHC(NH)NRH), amido (—C(O)NH$_2$);

C$_3$-C$_6$ cycloalkyl, optionally substituted with up to 6 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_6$ alkyl)NH$_2$), guanidine (—NHC(NH)NH$_2$), alkyl guanidine (—NHC(NH)NRH), amido (—C(O)NH$_2$);

C$_3$-C$_6$ heterocycloalkyl, optionally substituted with up to 4 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_6$ alkyl)NH$_2$), guanidine (—NHC(NH)NH$_2$), alkyl guanidine (—NHC(NH)NRH), amido (—C(O)NH$_2$);

C$_1$-C$_6$ alkenyl, optionally substituted with up to 4 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_6$ alkyl)NH$_2$), guanidine (—NHC(NH)NH$_2$), alkyl guanidine (—NHC(NH)NRH), amido (—C(O)NH$_2$);

C$_3$-C$_6$ cycloalkenyl, optionally substituted with up to 4 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_6$ alkyl)NH$_2$), guanidine (—NHC(NH)NH$_2$), alkyl guanidine (—NHC(NH)NRH), amido (—C(O)NH$_2$);

C$_3$-C$_6$ heterocycloalkenyl, optionally substituted with up to 4 of any of hydroxyl, halogen, thiol, cyano, nitro, oxo (═O), carboxyl, sulfonate, phosphate (—OPO$_3$H$_2$), alkylphosphate (—OPO$_3$RH), phosphonate (—PO$_3$H$_2$), alkylphosphonate (—PO$_3$RH), phosphinate (—PO$_2$H), alkylphosphinate (—PO$_2$R), amino, alkylamino (—NHR), dialkylamino (—NR$_2$), aminoalkyl (—(C$_1$-C$_6$ alkyl)NH$_2$), guanidine (—NHC(NH)NH₂), alkyl guanidine (—NHC(NH)NRH), amido (—C(O)NH₂);

C₆ aryl, optionally substituted with up to 4 of any of hydroxyl, halogen, thiol, cyano, nitro, carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₆ alkyl)NH₂), guanidine (—NHC(NH)NH₂), alkyl guanidine (—NHC(NH)NRH), amido (—C(O)NH₂);

C₃ to C₆ heteroaryl, optionally substituted with up to 4 of any of hydroxyl, halogen, thiol, cyano, nitro, carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂);

C₄ to C₆ heteroarylalkyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₆ alkyl)NH₂), guanidine (—NHC(NH)NH₂), alkyl guanidine (—NHC(NH)NRH), amido (—C(O)NH₂);

C₂ to C₆ alkynyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₆ alkyl)NH₂), guanidine (—NHC(NH)NH₂), alkyl guanidine (—NHC(NH)NRH), amido (—C(O)NH₂);

C₁ to C₆ heteroalkyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₂₀ alkyl)NH₂), guanidine (—NHC(NH)NH₂), alkyl guanidine (—NHC(NH)NRH), amido (—C(O)NH₂);

C₂ to C₆ heteroalkenyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₆ alkyl)NH₂), guanidine (—NHC(NH)NH₂), alkyl guanidine (—NHC(NH)NRH), amido (—C(O)NH₂); and C₂ to C₆ heteroalkynyl, optionally substituted with up to 4 of any of hydroxyl, halogen, thiol, cyano, nitro, oxo (═O), carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), amino, alkylamino (—NHR), dialkylamino (—NR₂), aminoalkyl (—(C₁-C₆ alkyl)NH₂), guanidine (—NHC(NH)NH₂), alkyl guanidine (—NHC(NH)NRH), amido (—C(O)NH₂), wherein each R is independently straight chain or branched C₁-C₂₀ alkyl, wherein at least two of D, E, F and G are carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), guanidine (—NHC(NH)NH₂), alkyl guanidine (—NHC(NH)NRH), and

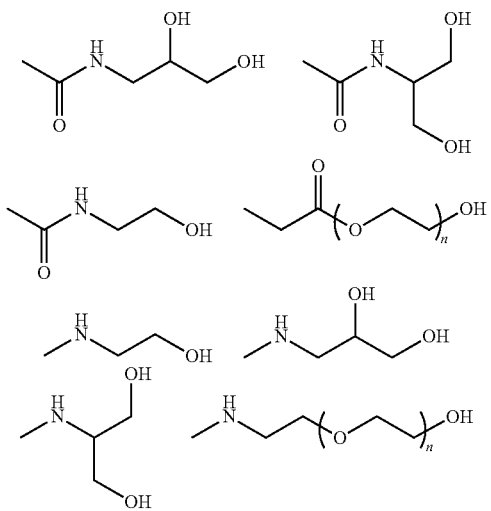

and wherein M is a paramagnetic metal ion.

2. A compound as claimed in claim 1, or a salt thereof, wherein:

each of D, E, F and G is selected from the group consisting of:

carboxyl, sulfonate, phosphate (—OPO₃H₂), alkylphosphate (—OPO₃RH), phosphonate (—PO₃H₂), alkylphosphonate (—PO₃RH), phosphinate (—PO₂H), alkylphosphinate (—PO₂R), guanidine (—NHC(NH)NH₂), alkyl guanidine (—NHC(NH)NRH), and

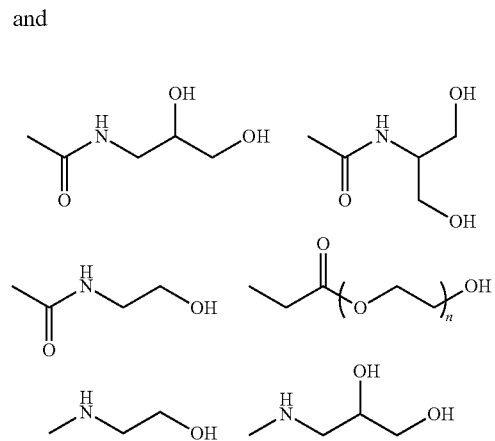

-continued

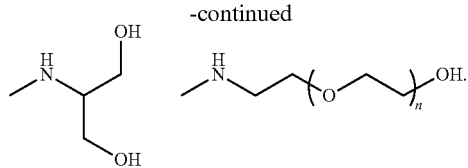

3. A compound as claimed in claim 2, or a salt thereof, wherein:
   each of D, E, F and G is carboxyl;
   each of $R^1$ to $R^8$ is hydrogen; and
   M is manganese.

4. A pharmaceutical formulation comprising a compound or salt thereof, as claimed in claim 1 and a pharmaceutically acceptable carrier, wherein the formulation is suitable for administration as an imaging enhancing agent and the contrast agent is present in an amount sufficient to enhance a magnetic resonance image.

5. A composition comprising a compound or salt thereof, as claimed in claim 1, and a pharmaceutically acceptable carrier, excipient or diluent, suitable for administration to a subject.

* * * * *